US009834779B2

(12) United States Patent
Yamaguchi et al.

(10) Patent No.: US 9,834,779 B2
(45) Date of Patent: Dec. 5, 2017

(54) METHOD FOR REGULATING EXPRESSION OF SPECIFIC PROTEIN USING PHOTORESPONSIVE TRANSCRIPTIONAL FACTOR, ISOPRENOID-PRODUCING PLANT HAVING GENE ENCODING PHOTORESPONSIVE TRANSCRIPTIONAL FACTOR INTRODUCED THEREINTO, AND METHOD FOR PRODUCING POLYISOPRENOID USING SAID ISOPRENOID-PRODUCING PLANT

(71) Applicant: SUMITOMO RUBBER INDUSTRIES, LTD., Kobe-shi, Hyogo (JP)

(72) Inventors: Haruhiko Yamaguchi, Kobe (JP); Yukino Inoue, Kobe (JP); Satoshi Kuroda, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 218 days.

(21) Appl. No.: 14/409,625

(22) PCT Filed: Jul. 3, 2013

(86) PCT No.: PCT/JP2013/068240
§ 371 (c)(1),
(2) Date: Dec. 19, 2014

(87) PCT Pub. No.: WO2014/007285
PCT Pub. Date: Jan. 9, 2014

(65) Prior Publication Data
US 2015/0322446 A1  Nov. 12, 2015

(30) Foreign Application Priority Data

Jul. 4, 2012 (JP) ................. 2012-150587

(51) Int. Cl.
*C12N 15/82* (2006.01)
*C12P 5/00* (2006.01)

(52) U.S. Cl.
CPC ..... *C12N 15/8237* (2013.01); *C12N 15/8243* (2013.01); *C12P 5/007* (2013.01)

(58) Field of Classification Search
None
See application file for complete search history.

(56) References Cited

U.S. PATENT DOCUMENTS

2004/0194162 A1  9/2004  Hahn et al.

FOREIGN PATENT DOCUMENTS

JP  2009-504138 A  2/2009

OTHER PUBLICATIONS

Rodríguez-Concepción et al., 2004, The Plant Cell 16: 144-156.*
Hiratsuka et al., 1994, The Plant Cell 6: 1805-1813.*
Maniatis et al., 1982, Molecular Cloning: A Laboratory Manual, Cold Spring Harbor Laboratory, pp. 324-343 and 387-389.*
Arabidopsis thaliana GT-1, GenBank sequence L36806, published May 16, 1995.*
Toledo-Ortiz et al., 2010, Proc. Natl. Acad. Sci. USA 107: 11626-11631.*
Jiao et al., 2007, Nature Genetics 8: 217-230.*
Botella-Pavia et al., "Regulation of carotenoid biosynthesis in plants: evidence for a key role of hydroxymethylbutenyl diphosphate reductase in controlling the supply of plastidial isoprenoid precursors," The Plant Journal, vol. 40, Issue 2, Oct. 2004, pp. 188-199.
Estévez et al., "1-Deoxy-D-xylulose-5-phosphate Synthase, a Limiting Enzyme for Plastidic Isoprenoid Biosynthesis in Plants," The Journal of Biological Chemistry, vol. 276, No. 25, Jun. 12, 2001 (Published, JBC Papers in Press: Mar. 22, 2001), pp. 22901-22909.
Gilmartin et al., "Molecular Light Switches for Plant Genes," The Plant Cell, vol. 2, May 1990, pp. 369-378.
Hao et al., "Laticifer Differentiation in Hevea brasiliensis: Induction by Exogenous Jasmonic Acid and Linolenic Acid," Annals of Botany, vol. 85, Issue 1, Jan. 2000, pp. 37-43.
Hiratsuka et al., "Molecular Dissection of GT-1 from Arabidopsis," The Plant Cell, vol. 6, Dec. 1994, pp. 1805-1813.
Kim et al., "A novel cDNA from Parthenium argentatum Gray enhances the rubber biosynthetic activity in vitro," Journal of Experimental Botany, vol. 55, No. 396, Feb. 2004 (Advanced Access publication: Jan. 12, 2004), pp. 377-385.
Post et al., "Laticifer-Specific cis-Prenyltransferase Silencing Affects the Rubber, Triterpene, and Inulin Content of Taraxacum brevicorniculatum," Plant Physiology, vol. 158, Mar. 2012, pp. 1406-1417.
Re et al., "Co-expression of native and introduced genes reveals cryptic regulation of HMG CoA reductase expression in Arabidopsis," The Plant Journal, vol. 7, No. 5, May 1995, pp. 771-784.
Rodríguez-Concepción et al., "Distinct Light-Mediated Pathways Regulate the Biosynthesis and Exchange of Isoprenoid Precursors during Arabidopsis Seedling Development," The Plant Cell, vol. 16, Jan. 2004, pp. 144-156.

(Continued)

*Primary Examiner* — Amjad Abraham
*Assistant Examiner* — Bratislav Stankovic
(74) *Attorney, Agent, or Firm* — Birch, Stewart, Kolasch & Birch, LLP

(57) ABSTRACT

The present invention provides a method for enhancing the overall pathway of polyisoprenoid biosynthesis. The present invention further provides an isoprenoid-producing plant having an overall enhanced pathway of polyisoprenoid biosynthesis, and a method for producing polyisoprenoids using such an isoprenoid-producing plant. The present invention relates to a method for regulating by a light-responsive transcription factor the expression of at least one protein selected from the group consisting of hydroxymethylglutaryl-CoA reductase, isopentenyl diphosphate isomerase, cis-prenyltransferase, and small rubber particle protein.

2 Claims, 1 Drawing Sheet

(56) References Cited

OTHER PUBLICATIONS

Rodríguez-Concepción, "Early steps in isoprenoid biosynthesis: Multilevel regulation of the supply of common precursors in plant cells," Phytochemistry Reviews, vol. 5, Issue 1, Feb. 2006, pp. 1-15.
Seibutsu-Kogaku Kaisha (Bioengineering), vol. 89, 2011, pp. 649-652, including English-language Concise Explanation.
Smalle et al., "The trihelix DNA-binding motif in higher plants is not restricted to the transcription factors GT-1 and GT-2," Proc. Natl. Acad. Sci. USA, vol. 95, Mar. 1998, pp. 3318-3322.
Venkatachalam et al., "Molecular cloning and characterization of a 3-hydroxy-3-methylglutaryl-coenzyme A reductase 1 (hmgr1) gene from rubber tree (*Hevea brasiliensis* Muell. Arg.): A key gene involved in isoprenoid biosynthesis," Physiol. Mol. Biol, Plants, vol. 15, No. 2, Apr. 2009, pp. 133-143.

\* cited by examiner

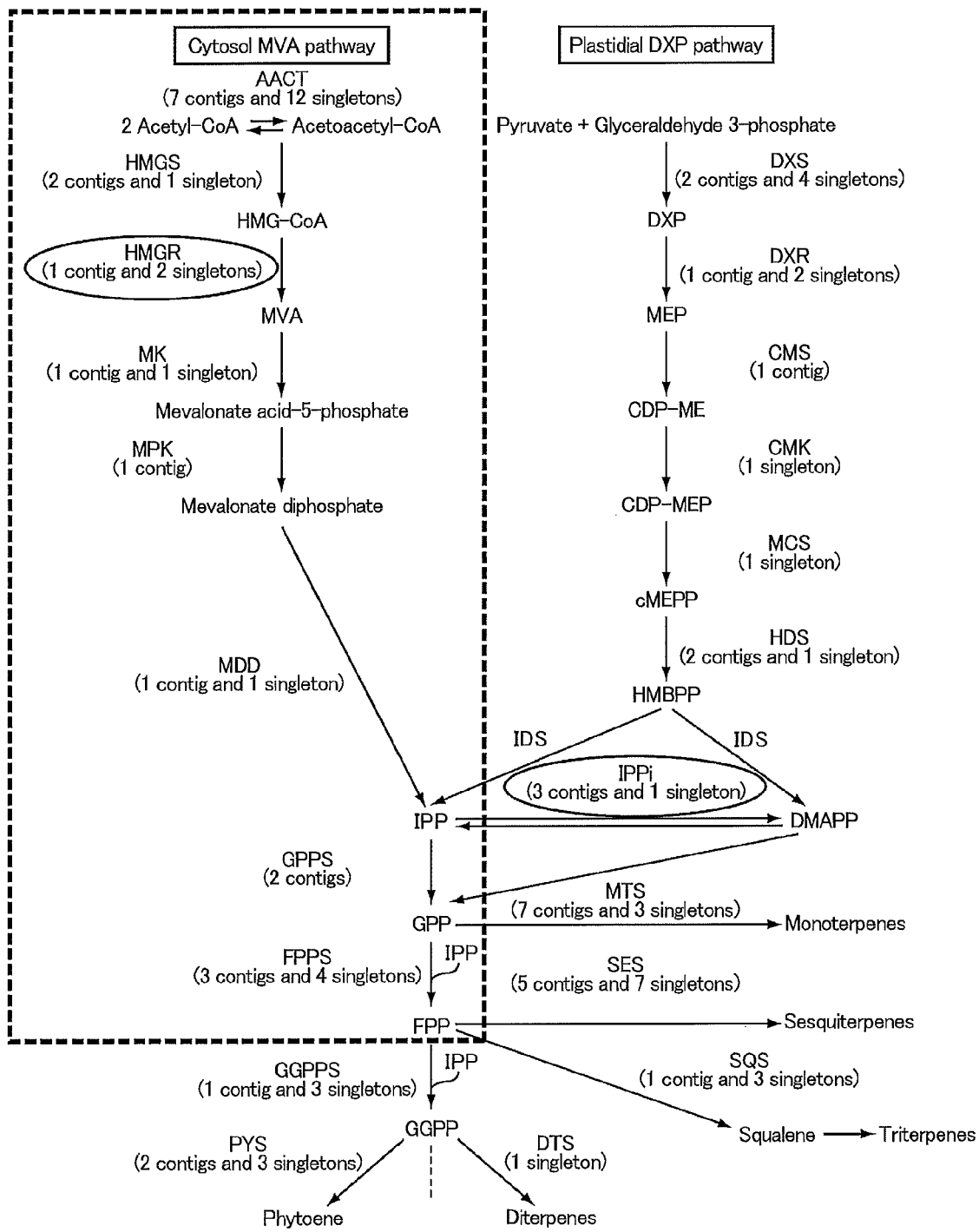

METHOD FOR REGULATING EXPRESSION OF SPECIFIC PROTEIN USING PHOTORESPONSIVE TRANSCRIPTIONAL FACTOR, ISOPRENOID-PRODUCING PLANT HAVING GENE ENCODING PHOTORESPONSIVE TRANSCRIPTIONAL FACTOR INTRODUCED THEREINTO, AND METHOD FOR PRODUCING POLYISOPRENOID USING SAID ISOPRENOID-PRODUCING PLANT

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "2015-07-24 5051-0341PUS1_ST25.txt" created on Jul. 24, 2015 and is 46,912 bytes in size. The sequence listing contained in this .txt file is part of the specification and is hereby incorporated by reference herein in its entirety.

TECHNICAL FIELD

The present invention relates to a method for regulating the expression of specific protein(s) by a light-responsive transcription factor, an isoprenoid-producing plant into which has been introduced a gene encoding a light-responsive transcription factor, and a method for producing polyisoprenoids using the isoprenoid-producing plant.

BACKGROUND ART

Nowadays natural rubber (one example of polyisoprenoids) for use in industrial rubber products can be harvested from rubber-producing plants, such as *Hevea brasiliensis* (Para rubber tree) belonging to the family Euphorbiaceae, or *Ficus elastica* (Indian rubber tree) belonging to the family Moraceae.

At present, *Hevea brasiliensis* is practically the only one source of natural rubber for industrial rubber products. *Hevea brasiliensis* is a plant that grows only in limited areas such as in Southeast Asia and South America. Moreover, *Hevea brasiliensis* requires about seven years from the time it is planted until it matures enough to allow rubber extraction, and the period during which natural rubber can be extracted is limited to 20 to 30 years. Although more natural rubber is expected to be needed, in particular, by developing countries in years to come, for the reason mentioned above it is difficult to greatly increase the production of natural rubber using *Hevea brasiliensis*. Depletion of natural rubber sources is therefore of concern and there are needs for stable natural rubber sources other than mature *Hevea brasiliensis* and for improvement in productivity of natural rubber from *Hevea brasiliensis*.

For example, an approach to improve productivity of natural rubber from *Hevea brasiliensis* is to extract more latex to produce more natural rubber. Specifically, such methods include stimulating the trunk of rubber trees with ethylene or ethephon (2-chloroethylphosphonic acid); and accelerating laticifer differentiation using lanolin containing jasmonic acid, linolenic acid (a precursor of jasmonic acid) or the like (see, for example, Non Patent Literature 1).

Unfortunately, if the method of increasing latex production via ethylene stimulation is applied to the trunk for a long term, then cracks may easily be generated in the bark thereof. In addition, the aim of the ethylene stimulation is to allow latex to exude more smoothly from laticifers and is not to directly improve the tree's ability to produce latex, and this method provides only a limited and insufficient increase in latex production.

Although jasmonic acid or the like can be used to accelerate laticifer differentiation and thereby increase the number of laticifers, this method also has the problem that latex exuding from laticifers can coagulate at the incision during the collection of latex by tapping, and therefore the produced latex may not be sufficiently collected.

Also known are attempts to promote biosynthesis of isoprenoid compounds in plants, such as by overexpressing a gene involved in the mevalonic acid (MVA) pathway or MEP pathway, which are pathways to isopentenyl diphosphate (IPP) biosynthesis, or a gene downstream in such a pathway (Non Patent Literatures 2 and 3).

These methods, however, only enhance the expression of specific enzymes involved in the above-mentioned pathways, or in other words, partially enhances the polyisoprenoid biosynthesis pathway, rather than enhancing the overall pathway of polyisoprenoid biosynthesis. Thus, there remains room for improvement in terms of enhancing the overall pathway of polyisoprenoid biosynthesis.

It is also known that some factors, including light responses, wound responses, and cold treatment, affect polyisoprenoid biosynthesis. However, it is not specifically known which transcription factor is activated in such a response to regulate polyisoprenoid biosynthesis.

CITATION LIST

Non Patent Literature

Non Patent Literature 1: Hao et al., Annals of Botany, 2000, Vol. 85, pp. 37-43
Non Patent Literature 2: Leon, P. et al., J. Biol. Chem. 276, 22901 (2001)
Non Patent Literature 3: Botella-Pavia, P. et al., Plant. J., 40, 188 (2004)

SUMMARY OF INVENTION

Technical Problem

The present invention was made to overcome the above problems, and an object of the present invention is to provide a method for enhancing the overall pathway of polyisoprenoid biosynthesis. Further objects of the present invention are to provide an isoprenoid-producing plant having an overall enhanced pathway of polyisoprenoid biosynthesis, and a method for producing polyisoprenoids using the isoprenoid-producing plant.

Solution to Problem

The present invention relates to a method for regulating by a light-responsive transcription factor the expression of at least one protein selected from the group consisting of hydroxymethylglutaryl-CoA reductase, isopentenyl diphosphate isomerase, cis-prenyltransferase, and small rubber particle protein.

Preferably, the method includes introducing a gene encoding the light-responsive transcription factor into a host to regulate the expression of the protein in the host.

The gene is preferably either of the following DNAs:
[1] a DNA having the base sequence of SEQ ID NO:1, 3, or 5; and

[2] a DNA encoding a protein with transcription factor activity and capable of hybridizing under stringent conditions to a DNA having a base sequence complementary to the base sequence of SEQ ID NO:1, 3, or 5.

The method is preferably used to enhance the expression of at least one protein selected from the group consisting of hydroxymethylglutaryl-CoA reductase, cis-prenyltransferase, and small rubber particle protein, and more preferably to enhance the expression of hydroxymethylglutaryl-CoA reductase, cis-prenyltransferase, and small rubber particle protein.

The light-responsive transcription factor is preferably any of the following proteins:
[1] a protein having the amino acid sequence of SEQ ID NO:2, 4, or 6;
[2] a protein having transcription factor activity and having a sequence that differs from the amino acid sequence of SEQ ID NO:2, 4, or 6 by one or more amino acid substitutions, deletions, insertions and/or additions; and
[3] a protein having transcription factor activity and having an amino acid sequence that has at least 80% sequence identity to the amino acid sequence of SEQ ID NO:2, 4, or 6.

The host is preferably an isoprenoid-producing plant.

The present invention also relates to an isoprenoid-producing plant, into which has been introduced a gene encoding a light-responsive transcription factor.

The gene is preferably either of the following DNAs:
[1] a DNA having the base sequence of SEQ ID NO:1, 3, or 5; and
[2] a DNA encoding a protein with transcription factor activity and capable of hybridizing under stringent conditions to a DNA having a base sequence complementary to the base sequence of SEQ ID NO:1, 3, or 5.

The present invention further relates to a method for producing polyisoprenoids using the isoprenoid-producing plant.

Advantageous Effects of Invention

The method of the present invention, which is for regulating by a light-responsive transcription factor the expression of at least one protein selected from the group consisting of hydroxymethylglutaryl-CoA reductase, isopentenyl diphosphate isomerase, cis-prenyltransferase, and small rubber particle protein, can enhance the overall pathway of polyisoprenoid biosynthesis. Moreover, the isoprenoid-producing plant of the present invention, into which has been introduced a gene encoding a light-responsive transcription factor, has an overall enhanced pathway of polyisoprenoid biosynthesis, and the use of the isoprenoid-producing plant in the production of polyisoprenoids allows increased polyisoprenoid production.

BRIEF DESCRIPTION OF DRAWINGS

FIG. 1 is a schematic view of a part of the polyisoprenoid biosynthesis pathway.

DESCRIPTION OF EMBODIMENTS

The present inventors have studied various ways to enhance the overall pathway of polyisoprenoid biosynthesis. FIG. 1 shows a part of the polyisoprenoid biosynthesis pathway. There are two known pathways for biosynthesis of isopentenyl diphosphate (IPP), which is an important member of the polyisoprenoid biosynthesis pathway: mevalonic acid (MVA) pathway (cytosol MVA pathway shown in FIG. 1); and MEP pathway (plastidial DXP pathway shown in FIG. 1).

The present inventors focused on the MVA pathway, which is considered to be a common pathway that supplies IPP in rubber latex synthesis, and selected, from various proteins involved in the polyisoprenoid biosynthesis pathway, some proteins that are expected to have important roles in view of enhancing the entire pathway enclosed in the dotted line in FIG. 1 or the entire downstream pathway.

Specifically, the following four proteins were selected: hydroxymethylglutaryl-CoA reductase (HMG-CoA reductase) that is a rate-limiting factor in the MVA pathway, which is a pathway to IPP biosynthesis; isopentenyl diphosphate isomerase (IPP isomerase) that is involved in isomerization of IPP; cis-prenyltransferase that is thought to be involved in isoprenoid chain elongation; and small rubber particle protein (SRPP) that is known to be involved in polyisoprenoid biosynthesis.

In order to simultaneously regulate the expression of the four proteins, that is, to comprehensively regulate the expression of the four proteins, the present inventors sought a transcription factor capable of regulating (or comprehensively regulating) the expression of all the four proteins. Specifically, DNA fragments from leaves of *Hevea brasiliensis* which contain genes (the base sequences of the genes encoding cis-prenyltransferase, HMG-CoA reductase, IPP isomerase, and SRPP are set forth in the sequence listing as SEQ ID NOs:7, 9, 11, and 13, respectively) encoding the four proteins (the amino acid sequences of cis-prenyltransferase, HMG-CoA reductase, IPP isomerase, and SRPP are set forth in the sequence listing as SEQ ID NOs:8, 10, 12, and 14, respectively) and their promoter regions were cloned (see EXAMPLES for details). The base sequences of the resulting DNA fragments were analyzed to reveal the base sequences of the promoter regions of the genes encoding the proteins.

Additionally, the revealed base sequences of the promoter regions of the four proteins were analyzed using a plant promoter database (a database of plant cis-acting regulatory DNA elements (PLACE)). The analysis revealed that the sequences contain many transcription factor binding sites involved in light responses and, in particular, the promoter regions of three genes (HMG-CoA reductase, IPP isomerase, SRPP), among the four genes analyzed, all contain a lot of GT1 consensus sequences (GRWAAW) to which GT1 (the base sequence and the amino acid sequence of GT1 from *Arabidopsis thaliana* are set forth in the sequence listing as SEQ ID NOs:1 and 2, respectively) binds. The number of GT1 consensus sequences is the highest for HMG-CoA reductase and the second highest for IPP isomerase and SRPP among the transcription factor binding sequences found in each case.

These results strongly suggest that the light-responsive transcription factor GT1 is a transcription factor capable of regulating the expression of all the four proteins, or in other words, a transcription factor capable of regulating the overall pathway of polyisoprenoid biosynthesis. Then a validation test using yeast cells was performed to confirm that the expression of the four proteins can be enhanced not only by the use of GT1 but also by the use of GTL1 (the base sequence and the amino acid sequence of GTL1 from *Arabidopsis thaliana* are set forth in the sequence listing as SEQ ID NOs:3 and 4, respectively) or GT2 (the base sequence and the amino acid sequence of GT2 from *Arabidopsis thaliana* are set forth in the sequence listing as SEQ ID NOs:5 and 6, respectively), which, similarly to GT1, are light-responsive transcription factors.

As described above, the present inventors have found that some light-responsive transcription factors including GT1 are capable of comprehensively enhancing the expression of HMG-CoA reductase, IPP isomerase, cis-prenyltransferase, and SRPP, and thus capable of enhancing the overall pathway of polyisoprenoid biosynthesis. Another finding is that since the light-responsive transcription factors including GT1 can enhance the overall pathway of polyisoprenoid biosynthesis, an isoprenoid-producing plant into which has been introduced a gene encoding any of the light-responsive transcription factors can be used in the production of polyisoprenoids to increase polyisoprenoid production.

Theoretically it is desirable to enhance the expression of HMG-CoA reductase, cis-prenyltransferase and SRPP while suppressing the expression of IPP isomerase. However, although the light-responsive transcription factors including GT1 enhance the expression of IPP isomerase as well as the expression of HMG-CoA reductase, cis-prenyltransferase and SRPP, polyisoprenoid production can be successfully increased because the overall pathway of polyisoprenoid biosynthesis is enhanced.

The term "hydroxymethylglutaryl-CoA reductase" (HMG-CoA reductase) as used herein refers to a rate-limiting enzyme of the mevalonic acid pathway and is intended to include both hydroxymethylglutaryl-CoA reductase (NADPH) (EC 1.1.1.34) and hydroxymethylglutaryl-CoA reductase (EC 1.1.1.88).

The term "isopentenyl diphosphate isomerase" (IPP isomerase) as used herein refers to an enzyme that catalyzes the isomerization between isopentenyl diphosphate (IPP) and its isomer, dimethylallyl pyrophosphate (DMAPP).

The term "cis-prenyltransferase" as used herein refers to an enzyme that catalyzes cis-chain elongation of isoprenoid compounds.

The term "small rubber particle protein" (SRPP) as used herein refers to a small rubber particle-associated protein which binds to small rubber particles of 10 μm or less in diameter in the latex of *Hevea brasiliensis* or the like.

The method of the present invention is for regulating by a light-responsive transcription factor the expression of at least one protein selected from the group consisting of hydroxymethylglutaryl-CoA reductase, isopentenyl diphosphate isomerase, cis-prenyltransferase, and small rubber particle protein.

The light-responsive transcription factor is not particularly limited, provided that it is a transcription factor that can be activated in response to light. Examples include transcription factors of the GT family such as GT1 (the base sequence and the amino acid sequence of GT1 from *Arabidopsis thaliana* are set forth in the sequence listing as SEQ ID NOs:1 and 2, respectively), GTL1 (the base sequence and the amino acid sequence of GTL1 from *Arabidopsis thaliana* are set forth in the sequence listing as SEQ ID NOs:3 and 4, respectively), and GT2 (the base sequence and the amino acid sequence of GT2 from *Arabidopsis thaliana* are set forth in the sequence listing as SEQ ID NOs:5 and 6, respectively), as well as members of the following transcription factors: G-box-binding factors, TGACG-binding proteins, 1-box-binding proteins, AT-rich-binding proteins, and box one factors.

The term "transcription factor" as used herein refers to a protein having an activity of increasing or decreasing (preferably increasing) the rate of transcription of a gene or genes.

The origin of the light-responsive transcription factor is not particularly limited, but preferred are transcription factors from *Hevea brasiliensis, Sonchus oleraceus, Parthenium argentatum, Taraxacum koksaghyz*, or *Arabidopsis thaliana*.

(Amino Acid Sequence of Light-Responsive Transcription Factor)

The following protein [1] is a specific example of the light-responsive transcription factor:

[1] a protein having the amino acid sequence of SEQ ID NO:2, 4, or 6.

Moreover, it is known that some transcription factors have transcription factor activity even when one or more amino acid substitutions, deletions, insertions, or additions are introduced into their original amino acid sequences. Considering this fact, the following protein [2] may also be mentioned as a specific example of the light-responsive transcription factor:

[2] a protein having transcription factor activity and having a sequence that differs from the amino acid sequence of SEQ ID NO:2, 4, or 6 by one or more amino acid substitutions, deletions, insertions and/or additions.

The term "transcription factor activity" as used herein refers to an activity of increasing or decreasing (preferably increasing) the rate of transcription of at least one gene selected from the group consisting of genes encoding hydroxymethylglutaryl-CoA reductase, isopentenyl diphosphate isomerase, cis-prenyltransferase, and small rubber particle protein.

In terms of maintaining transcription factor activity, the number of amino acid substitutions, deletions, insertions, and/or additions introduced in the amino acid sequence of SEQ ID NO:2 is preferably 1 or more, more preferably 1 to 81, still more preferably 1 to 61, particularly preferably 1 to 40, most preferably 1 to 20, even most preferably 1 to 8, and still even most preferably 1 to 4.

Also in terms of maintaining transcription factor activity, the number of amino acid substitutions, deletions, insertions, and/or additions introduced in the amino acid sequence of SEQ ID NO: 4 is preferably 1 or more, more preferably 1 to 134, still more preferably 1 to 100, particularly preferably 1 to 67, most preferably 1 to 33, even most preferably 1 to 13, and still even most preferably 1 to 7.

Also in terms of maintaining transcription factor activity, the number of amino acid substitutions, deletions, insertions, and/or additions introduced in the amino acid sequence of SEQ ID NO: 6 is preferably 1 or more, more preferably 1 to 115, still more preferably 1 to 86, particularly preferably 1 to 58, most preferably 1 to 29, even most preferably 1 to 12, and still even most preferably 1 to 6.

Among other amino acid substitutions, conservative substitutions are preferred. Specific examples thereof include substitutions within each of the following groups in the parentheses: (glycine, alanine), (valine, isoleucine, leucine), (aspartic acid, glutamic acid), (asparagine, glutamine), (serine, threonine), (lysine, arginine) and (phenylalanine, tyrosine).

The amino acid substitutions, deletions, insertions, and/or additions are preferably introduced into regions other than light-responsive transcription factor activity domains, domains linked to transcription factor binding sites, and other important parts involved in transcription factor activity. Those skilled in the art can appropriately identify such domains by sequence homology analysis with a known light-responsive transcription factor.

It is also known that some proteins with amino acid sequences that have high sequence identity to the amino acid sequence of a transcription factor also have similar activity. Considering this fact, the following protein [3] may also be mentioned as a specific example of the light-responsive transcription factor:

[3] a protein having transcription factor activity and having an amino acid sequence that has at least 80% sequence identity to the amino acid sequence of SEQ ID NO:2, 4, or 6.

In terms of maintaining transcription factor activity, the sequence identity to the amino acid sequence of SEQ ID NO:2, 4, or 6 is preferably at least 85%, more preferably at least 90%, still more preferably at least 95%, particularly preferably at least 98%, and most preferably at least 99%.

The sequence identity between amino acid sequences or base sequences can be determined using the algorithm BLAST® [Pro. Natl. Acad. Sci. USA, 90, 5873 (1993)] developed by Karlin and Altschul or FASTA [Methods Enzymol., 183, 63 (1990)].

Whether a protein has transcription factor activity may be determined by known techniques, such as gel shift assays, or reporter assays using a reporter gene encoding β-galactosidase, luciferase, GFP (green fluorescent protein) or the like.

The light-responsive transcription factor is preferably any of the following proteins:
[1-1] a protein having the amino acid sequence of SEQ ID NO:2 or 4;
[2-1] a protein having transcription factor activity and having a sequence that differs from the amino acid sequence of SEQ ID NO:2 or 4 by one or more amino acid substitutions, deletions, insertions, and/or additions; and
[3-1] a protein having transcription factor activity and having an amino acid sequence that has at least 80% sequence identity to the amino acid sequence of SEQ ID NO:2 or 4.

The light-responsive transcription factor is more preferably any of the following proteins:
[1-2] a protein having the amino acid sequence of SEQ ID NO:2;
[2-2] a protein having transcription factor activity and having a sequence that differs from the amino acid sequence of SEQ ID NO:2 by one or more amino acid substitutions, deletions, insertions, and/or additions; and
[3-2] a protein having transcription factor activity and having an amino acid sequence that has at least 80% sequence identity to the amino acid sequence of SEQ ID NO:2.

(DNA Encoding Light-Responsive Transcription Factor)

Moreover, the DNA encoding the light-responsive transcription factor may be either of the following DNAs [1] and [2]:
[1] a DNA having the base sequence of SEQ ID NO:1, 3, or 5; and
[2] a DNA encoding a protein with transcription factor activity and capable of hybridizing under stringent conditions to a DNA having a base sequence complementary to the base sequence of SEQ ID NO:1, 3, or 5.

In this context, the term "hybridizing" means a process in which the DNA hybridizes to a DNA having a particular base sequence or a part of the DNA. Thus, the DNA having a particular base sequence or the part of the DNA may have a base sequence long enough to be usable as a probe in Northern or Southern blot analysis or as an oligonucleotide primer in polymerase chain reaction (PCR) analysis. The DNA used as a probe may have a length of at least 100 bases, preferably at least 200 bases, and more preferably at least 500 bases although it may be a DNA of at least 10 bases, and preferably of at least 15 bases in length.

Techniques to perform DNA hybridization experiments are well known. The hybridization conditions under which experiments are performed can be determined according to, for example, Molecular Cloning, 2nd ed. and 3rd ed. (2001), Methods for General and Molecular Bacteriology, ASM Press (1994), Immunology methods manual, Academic press (Molecular), and many other standard textbooks.

The stringent conditions may include, for example, an overnight incubation at 42° C. of a DNA-immobilized filter and a DNA probe in a solution containing 50% formamide, 5×SSC (750 mM sodium chloride and 75 mM sodium citrate), 50 mM sodium phosphate (pH 7.6), 5×Denhardt's solution, 10% dextran sulfate, and 20 µg/l denatured salmon sperm DNA, followed by washing the filter for example in a 0.2×SSC solution at approximately 65° C. Less stringent conditions may also be used. Changes in the stringency may be accomplished through the manipulation of formamide concentration (lower percentages of formamide result in lower stringency), salt concentrations or temperature. For example, low stringent conditions include an overnight incubation at 37° C. in a solution containing 6×SSCE (20×SSCE: 3 mol/l sodium chloride, 0.2 mol/l sodium dihydrogen phosphate, and 0.02 mol/l EDTA, pH 7.4), 0.5% SDS, 30% formamide, and 100 µg/l denatured salmon sperm DNA, followed by washing in a 1×SSC solution containing 0.1% SDS at 50° C. In addition, to achieve even lower stringency, washes performed following hybridization under the above-mentioned low stringent conditions may be done at higher salt concentrations (e.g. 5×SSC).

Variations in the above various conditions may be accomplished through the inclusion or substitution of blocking reagents used to suppress background in hybridization experiments. The inclusion of blocking reagents may require modification of the hybridization conditions for compatibility.

The DNA capable of hybridization under stringent conditions described above may be a DNA having a base sequence that has at least 80%, preferably at least 90%, more preferably at least 95%, even more preferably at least 98%, and particularly preferably at least 99% sequence identity to the base sequence of SEQ ID NO: 1, 3, or 5 as calculated using a program such as BLAST® or FASTA with the parameters.

Whether the DNA capable of hybridizing under stringent conditions to a DNA mentioned above encodes a protein with transcription factor activity may be determined by known techniques, such as gel shift assays or reporter assays using a reporter gene encoding β-galactosidase, luciferase, GFP (green fluorescent protein) or the like.

The DNA encoding the light-responsive transcription factor is preferably either of the following DNAs:
[1-1] a DNA having the base sequence of SEQ ID NO:1 or 3; and
[2-1] a DNA encoding a protein with transcription factor activity and capable of hybridizing under stringent conditions to a DNA having a base sequence complementary to the base sequence of SEQ ID NO:1 or 3.

More preferred is either of the following DNAs:
[1-1] a DNA having the base sequence of SEQ ID NO:1; and
[2-1] a DNA encoding a protein with transcription factor activity and capable of hybridizing under stringent conditions to a DNA having a base sequence complementary to the base sequence of SEQ ID NO:1.

The light-responsive transcription factor and the DNA encoding the light-responsive transcription factor can be obtained by site-directed mutagenesis of, for example, any of the base sequences of SEQ ID NOs:1, 3, and 5 (the base sequence of GT1 from *Arabidopsis thaliana*, the base sequence of GTL1 from *Arabidopsis thaliana*, and the base sequence of GT2 from *Arabidopsis thaliana*) according to site-directed mutagenesis techniques described in Molecular Cloning, A Laboratory Manual, Second Edition, Cold Spring Harbor Laboratory Press (1989), Current Protocols in Molecular Biology, John Wiley & Sons (1987-1997), Nucleic Acids Research, 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci. USA, 82, 488 (1985), etc.

(Transformant)

The gene encoding the light-responsive transcription factor can be introduced into a host to provide an organism (transformant) that is transformed to express the light-responsive transcription factor. This transformant expresses the light-responsive transcription factor and is thereby capable of the regulated (enhanced) expression of at least one protein selected from the group consisting of hydroxymethylglutaryl-CoA reductase, isopentenyl diphosphate isomerase, cis-prenyltransferase, and small rubber particle protein (preferably at least one protein selected from the group consisting of hydroxymethylglutaryl-CoA reductase, cis-prenyltransferase, and small rubber particle protein).

More specifically, the transformant is capable of the comprehensively enhanced expression of the four proteins: hydroxymethylglutaryl-CoA reductase, isopentenyl diphosphate isomerase, cis-prenyltransferase, and small rubber particle protein (preferably the three proteins: hydroxymethylglutaryl-CoA reductase, cis-prenyltransferase, and small rubber particle protein). Therefore, the transformant has an overall enhanced pathway of polyisoprenoid biosynthesis and is capable of increased polyisoprenoid production.

The following briefly describes how to prepare an organism (transformant) that is transformed to express a light-responsive transcription factor. The brief description below mainly focuses on how to prepare a transformant that is transformed to express the above-mentioned light-responsive transcription factor. Once a gene to be introduced which encodes the light-responsive transcription factor has been determined, such a transformant can be prepared by known methods.

Specifically, for example, a DNA containing the base sequence of SEQ ID NO:1, 3, or 5 (the base sequence of GT1 from *Arabidopsis thaliana*, the base sequence of GTL1 from *Arabidopsis thaliana*, or the base sequence of GT2 from *Arabidopsis thaliana*) is inserted downstream of a promoter of an appropriate expression vector using appropriate restriction enzymes and the like to prepare a recombinant DNA, which is then introduced into host cells compatible with the expression vector to give a transformant.

Although the above description relates to the case where a DNA containing the base sequence of SEQ ID NO: 1, 3, or 5 (the base sequence of GT1 from *Arabidopsis thaliana*, the base sequence of GTL1 from *Arabidopsis thaliana*, or the base sequence of GT2 from *Arabidopsis thaliana*) is used, a DNA encoding any of other light-responsive transcription factors from *Arabidopsis thaliana* or light-responsive transcription factors from organisms other than *Arabidopsis thaliana* may be used. In such cases, screening may be performed by known methods, such as using a part of the base sequence of SEQ ID NO:1 as a probe, to identify and isolate a DNA encoding a particular light-responsive transcription factor. The method for isolating a DNA molecule of interest using a DNA molecule as a probe is described in, for example, Molecular Cloning, 2nd edition, Cold Spring Harbor Press (1989). DNAs obtained by mutagenesis of the DNA may also be used.

Any of microorganisms, yeasts, animal cells, insect cells, plant cells, and the like can be used as the host (host cells), as long as they are capable of expressing a gene of interest. Since the only organisms currently known to biosynthesize polyisoprenoids are plants (isoprenoid-producing plants), the host is preferably a plant (an isoprenoid-producing plant), and the host cells are preferably plant cells (cells of an isoprenoid-producing plant). Please note that if a future advance in technology allows cells other than plant cells to biosynthesize polyisoprenoids, the gene encoding the light-responsive transcription factor can be suitably introduced into such cells.

The isoprenoid-producing plant is not particularly limited, provided that it is capable of producing isoprenoids. Examples include plants of the genus *Hevea*, such as *Hevea brasiliensis*; plants of the genus *Sonchus*, such as *Sonchus oleraceus*, *Sonchus asper*, and *Sonchus brachyotus*; plants of the genus *Solidago*, such as *Solidago altissima*, *Solidago virgaurea* subsp. *asiatica*, *Solidago virgaurea* subsp. *leipcarpa*, *Solidago virgaurea* subsp. *leipc arpaf. paludosa*, *Solidago virgaurea* subsp. *gigantea*, and *Solidago gigantea* Ait. var. *leiophylla* Fernald; plants of the genus *Helianthus*, such as *Helianthus annuus*, *Helianthus argophyllus*, *Helianthus atrorubens*, *Helianthus debilis*, *Helianthus decapetalus*, and *Helianthus giganteus*; plants of the genus *Taraxacum*, such as *Taraxacum*, *Taraxacum venustum* H. Koidz, *Taraxacum hondoense* Nakai, *Taraxacum platycarpum* Dahlst, *Taraxacum japonicum*, *Taraxacum officinale* Weber, and *Taraxacum koksaghyz*; plants of the genus *Ficus*, such as *Ficus carica*, *Ficus elastica*, *Ficus pumila* L., *Ficus erecta* Thumb., *Ficus ampelas* Burm. f., *Ficus benguetensis* Merr., *Ficus irisana* Elm., *Ficus microcarpa* L.f., *Ficus septica* Burm. f., and *Ficus benghalensis*; plants of the genus *Parthenium*, such as *Parthenium argentatum*, *Parthenium hysterophorus*, and *Parthenium hysterophorus*; and *Lactuca serriola* and *Ficus benghalensis*. In particular, the isoprenoid-producing plant is preferably at least one selected from the group consisting of plants of the genera *Hevea*, *Sonchus*, *Taraxacum* and *Parhenium*, and more preferably at least one selected from the group consisting of *Hevea brasiliensis*, *Sonchus oleraceus*, *Parthenium argentatum*, and *Taraxacum koksaghyz*.

Examples of expression vectors that can be used include vectors that are capable of autonomous replication in the host cells or of being incorporated into a chromosome thereof and contain a promoter at a position that permits transcription of the recombinant DNA.

In the case where plant cells are used as host cells, a pBI vector, a pUC vector, a Ti plasmid or tobacco mosaic virus vector, for example, may be used as an expression vector.

Any promoter that functions in the plant cells can be used. Examples thereof include cauliflower mosaic virus (CaMV) 35S promoter and rice actin-1 promoter, nopaline synthase gene promoter, tobacco mosaic virus 35S promoter, and rice actin gene promoter.

Preferred are expression vectors containing a promoter that is specifically expressed in a tissue in which isoprenoid compounds are biosynthesized, such as laticifers. When it is specifically expressed in a tissue in which polyisoprenoids are biosynthesized, retardation of plant growth and other adverse effects can be prevented.

The recombinant vector can be introduced by any techniques to introduce a DNA into plant cells. Examples include techniques using *Agrobacterium* (JP S59-140885 A, JP S60-70080 A, WO94/00977), electroporation (JP S60-251887 A), and techniques using a particle gun (gene gun) (JP 2606856 B, JP 2517813 B).

A transformant (transgenic plant cells) into which has been introduced the gene encoding the light-responsive transcription factor can be prepared by these techniques and the like.

The present invention provides an isoprenoid-producing plant into which has been introduced a gene encoding a light-responsive transcription factor. The isoprenoid-producing plant is not particularly limited, as long as it is an isoprenoid-producing plant including transgenic plant cells. The isoprenoid-producing plant is intended to include, for example, in addition to transgenic plant cells prepared by the above-described techniques, their progeny or clones, and even progeny plants obtained by passaging these cells. Once transgenic plant cells into which the DNA or vector has been introduced in the genome are obtained, progeny or clones can be obtained from the transgenic plant cells by sexual or asexual reproduction, tissue culture, cell culture, cell fusion, or the like. Further, the transgenic plant cells, or progeny or clones thereof may be used to obtain reproductive materials (e.g. seeds, fruits, cuttings, stem tubers, root tubers, shoots, adventitious buds, adventitious embryos, calluses, protoplasts) which can be used to produce the isoprenoid-producing plant on a large scale.

Techniques to regenerate a plant from transgenic plant cells are already known; for example, Doi et al. disclose a technique for *eucalyptus* (Japanese Patent Application No. H11-127025), Fujimura et al. disclose a technique for rice (Fujimura et al., (1995), Plant Tissue Culture Lett., vol. 2: p 74-), Shillito et al. disclose a technique for corn (Shillito et al., (1989), Bio/Technology, vol. 7: p 581-), Visser et al. discloses a technique for potato (Visser et al., (1989), Theor. Appl. Genet., vol. 78: p 589-), and Akama et al. disclose a technique for *Arabidopsis thaliana* (Akama et al., (1992), Plant Cell Rep., vol. 12: p 7-). Those skilled in the art can regenerate a plant from transgenic plant cells according to these publications.

Whether a target transcription factor gene is expressed in a regenerated plant can be determined by well-known techniques. For example, western blot analysis may be used to assess the expression of a target transcription factor.

Seeds can be obtained from the transgenic plant, for example, as follows: the transgenic plant is rooted in an appropriate medium and then transplanted to water-containing soil in a pot, and grown under proper cultivation conditions so as to finally produce seeds, which are then collected. Further, plants can be grown from seeds, for example, as follows: seeds obtained from the transgenic plant as described above are sown in water-containing soil, and grown under proper cultivation conditions into plants.

The present invention makes use of the isoprenoid-producing plant into which has been introduced a gene encoding a light-responsive transcription factor in the production of polyisoprenoids to increase polyisoprenoid production. Specifically, polyisoprenoids can be produced by culturing transgenic plant cells prepared as described above, calluses obtained from such transgenic plant cells, cells redifferentiated from such calluses, or the like in an appropriate medium, or by growing a transgenic plant regenerated from the transgenic plant cells, a plant grown from a seed collected from such a transgenic plant, or the like under proper cultivation conditions. The isoprenoid-producing plant of the present invention has a polyisoprenoid biosynthesis pathway that is overall enhanced by the light-responsive transcription factor introduced therein, and is thereby capable of increased polyisoprenoid production.

The term "polyisoprenoid" as used herein is a generic term used to refer to polymers having isoprene ($C_5H_8$) units. Examples of polyisoprenoids include polymers such as monoterpene ($C_{10}$), sesquiterpene ($C_{15}$), diterpene ($C_{20}$), sesterterpene ($C_{25}$), triterpene ($C_{30}$), tetraterpene ($C_{40}$), and natural rubber.

The present invention enables to regulate (enhance) by a light-responsive transcription factor the expression of at least one protein selected from the group consisting of hydroxymethylglutaryl-CoA reductase, isopentenyl diphosphate isomerase, cis-prenyltransferase, and small rubber particle protein, as described above, and thus makes it possible to enhance the overall pathway of polyisoprenoid biosynthesis to increase polyisoprenoid production.

The isoprenoid-producing plant of the present invention into which has been introduced a gene encoding a light-responsive transcription factor has an overall enhanced pathway of polyisoprenoid biosynthesis, and the use of the isoprenoid-producing plant in the production of polyisoprenoids allows increased polyisoprenoid production.

As described above, the method of the present invention, the isoprenoid-producing plant of the present invention, and the method for producing polyisoprenoids of the present invention, all of which are capable of increasing polyisoprenoid production, can be effective for natural rubber source depletion that is of concern.

EXAMPLES

The present invention will be specifically described by reference to examples. The examples are not to be construed as limiting the present invention.

(Preparation of Promoter Sequence)

DNA fragments containing the gene encoding HMG-CoA reductase, IPP isomerase, cis-prenyltransferase, or small rubber particle protein from leaves of *Hevea brasiliensis* (the base sequences of cis-prenyltransferase, HMG-CoA reductase, IPP isomerase, and SRPP are set forth in the sequence listing as SEQ ID NOs:7, 9, 11, and 13, respectively) and its promoter were cloned in the following manner. First, genomic DNA was extracted from leaves of *Hevea brasiliensis*. The extraction was accomplished using a commercial genomic DNA extraction kit. The genes with their promoters were amplified by TAIL-PCR using random primers shown as Primers 1 to 6 and primers corresponding to the genes.

```
                                              (SEQ ID NO: 15)
    Primer 1: 5'-ntcgastwtsgwgtt-3'

(SEQ ID NO: 16)
    Primer 2: 5'-ngtcgtswganawgaa-3'

(SEQ ID NO: 17)
    Primer 3: 5'-wgtgnagwancanag-3'

(SEQ ID NO: 18)
    Primer 4: 5'-sttntastnctntgc-3'

(SEQ ID NO: 19)
    Primer 5: 5'-sstggstanatwatwct-3'

(SEQ ID NO: 20)
    Primer 6: 5'-agwgnagwancanaga-3'
```

The base sequences of the DNA fragments obtained using the primers were analyzed to determine the presence of the promoter sequences of HMG-CoA reductase, IPP isomerase, cis-prenyltransferase, and small rubber particle protein. The base sequences of the promoter sequences of HMG-CoA reductase, IPP isomerase, cis-prenyltransferase, and small rubber particle protein are shown as SEQ ID NOs: 21 to 24, respectively.

The promoter sequences were analyzed using a plant promoter database (a database of plant cis-acting regulatory DNA elements (PLACE)).

The analysis revealed that the sequences contain many transcription factor binding sites involved in light responses, and, in particular, the promoter sequences of three genes (HMG-CoA reductase, IPP isomerase, and small rubber particle protein), among the four genes analyzed, all contain a lot of GT1 consensus sequences (GRWAAW) to which GT1 binds. The number of GT1 consensus sequences is the highest for HMG-CoA reductase and the second highest for IPP isomerase and small rubber particle protein among the transcription factor binding sequences found in each case.

(Amplification of Promoter Region)

As the promoter regions of the genes, the following regions were amplified by PCR.
HMG-CoA reductase promoter: −1 to −1500 bp, −1 to −1000 bp, and −1 to −500 bp
IPP isomerase promoter: −1 to −1000 bp, and −1 to −500 bp
Cis-prenyltransferase promoter: −1 to −500 bp
Small rubber particle protein promoter: −1 to −1000 bp, and −1 to −500 bp The PCR products were each cloned into pMD20T (Takara Bio, Inc.) to construct pMD20T-hmgpro (−1500), pMD20T-hmgpro (−1000), pMD20T-hmgpro (−500), pMD20T-ipppro (−1000), pMD20T-ipppro (−500), pMD20T-cptpro (−500), pMD20T-srpppro (−1000), and pMD20T-srpppro (−500). The sequences of the inserted PCR products were analyzed to confirm that no mutation was introduced.

(Construction of Reporter Sequence-Containing Vector)

The plasmids constructed in (Amplification of promoter region) were restricted with SpeI and any of HindIII, KpnI and BamHI, and the promoter sequence fragments were individually incorporated at a site of pYES3/CT/LacZ from which the T7 promoter region had been removed, that is, immediately upstream of the lacZ reporter gene to construct pYES3-hmgprolacZ (−1500), pYES3-hmgprolacZ (−1000), pYES3-hmgpro (−500), pYES3-ippprolacZ (−1000), pYES3-ippprolacZ (−500), pYES3-cptprolacZ (−500), pYES3-srppprolacZ (−1000), and pYES3-srppprolacZ (−500). Ligation high ver. 2 (TOYOBO) was used for ligation.

(Construction of Vector for Gene Introduction into Yeast Chromosome)

The sequence from the SpeI site to the CYC1 transcription termination signal of each of the plasmids constructed in (Construction of reporter sequence-containing vector) was amplified by PCR, and each fragment was treated with the restriction enzyme SalI, SmaI, XbaI or SphI, thereby providing DNA fragments with the promoter sequences each linked to the lacZ gene. In order to allow the obtained DNA fragments to be inserted into a yeast chromosome, the DNA fragments were individually incorporated into pAUR101 DNA (Takara Bio, Inc.) treated with the same restriction enzymes to construct pAUR101-hmgprolacZ (−1500), pAUR101-hmgprolacZ (−1000), pAUR101-hmgpro (−500), pAUR101-ippprolacZ (−1000), pAUR101-ippprolacZ (−500), pAUR101-cptprolacZ (−500), pAUR101-srpppro-lacZ (−1000), and pAUR101-srppprolacZ (−500). Ligation high ver.2 was used for ligation as above.

(Acquisition of Transcription Factor Gene)

Next, PCR was performed using an *Arabidopsis thaliana* cDNA library as a template. The PCR produced the following three PCR fragments: At1g13450 (GT1) (SEQ ID NO:1), At1g76890 (GT2) (SEQ ID NO:5), and At1g33240 (GTL1) (SEQ ID NO:3). The obtained PCR products were each cloned into pMD20T to construct pMD20T-GT1, pMD20T-GT2, and pMD20T-GTL1. The sequences of the inserted PCR products were analyzed to confirm that no mutation was introduced.

(Construction of Transcription Factor Expression Vector)

The plasmids constructed in (Acquisition of transcription factor gene) were restricted with SpeI, BamHI, or EcoRV, and the transcription factor genes were individually incorporated downstream of the TEF1 promoter region of p427TEF (COSMO BIO Co., Ltd.), whereby pTEF-GT1, pTEF-GT2, and pTEF-GTL1 were constructed. Ligation high ver.2 was used for ligation.

(Transformation of Yeast)

The plasmids constructed in (Construction of vector for gene introduction into yeast chromosome) and (Construction of transcription factor expression vector) were introduced into yeast cells (BY4741 strain) by electroporation. Screening for transgenic yeast cells was carried out by culturing yeast cells on a medium containing the antifungal antibiotics Aureobasidin A (Takara Bio, Inc.) and G418 (Wako Pure Chemical Industries, Ltd.).

(Demonstration of Effect of Transcription Factor)

The transgenic yeast cells were cultured on a medium containing X-gal to assess the expression of lacZ due to transcription factor activity. Specifically, when the lacZ reporter gene, which is linked to each promoter sequence, is expressed, X-gal in the medium is then decomposed to develop a blue color. Based on this mechanism, when the medium turned blue, it was determined that lacZ was expressed due to transcription factor activity. This test was repeated 10 times. Table 1 shows how many times lacZ was expressed due to transcription factor activity.

TABLE 1

| | Transcription factor | | | |
|---|---|---|---|---|
| Promoter sequence | At1g13450 (GT1) | At1g76890 (GT2) | At1g33240 (GTL1) | Control (No transcription factor) |
| hmg(−1500) | 8 | 5 | 6 | 0 |
| hmg(−1000) | 7 | 3 | 4 | 0 |
| hmg(−500) | 3 | 1 | 1 | 0 |
| ipp(−1000) | 7 | 5 | 2 | 0 |
| ipp(−500) | 2 | 1 | 0 | 0 |
| cpt(−500) | 2 | 2 | 1 | 0 |
| srpp(−1000) | 7 | 5 | 4 | 0 |
| srpp(−500) | 2 | 2 | 1 | 0 |

Number of yeast cells that exhibited reporter gene activity (N = 10)

Table 1 shows that the use of At1g13450 (GT1) (SEQ ID NOs: 1 and 2), At1g76890 (GT2) (SEQ ID NOs: 5 and 6), or At1g33240 (GTL1) (SEQ ID NOs:3 and 4), particularly At1g13450 (GT1), enhanced the reporter gene activity. Moreover, At1g13450(GT1), At1g76890 (GT2), and At1g33240 (GTL1) have proved to function as transcription factors for HMG-CoA reductase, IPP isomerase, cis-prenyltransferase, and small rubber particle because the longer the promoter sequence was, the more often the reporter gene activity was expressed, or, in other words, the higher number of At1g13450 (GT1), At1g76890 (GT2), or At1g33240 (GTL1)-binding sites the promoter sequence contained, the more often the reporter gene activity was expressed. These results demonstrate that by introducing At1g13450 (GT1), At1g76890 (GT2), or At1g33240 (GTL1), particularly At1g13450 (GT1), into an isoprenoid-producing plant, the overall pathway of polyisoprenoid biosynthesis can be enhanced to increase polyisoprenoid production.

(Sequence Listing Free Text)
SEQ ID NO: 1: base sequence of GT1-encoding gene from *Arabidopsis thaliana*
SEQ ID NO:2: amino acid sequence of GT1 from *Arabidopsis thaliana*
SEQ ID NO:3: base sequence of GTL1-encoding gene from *Arabidopsis thaliana*
SEQ ID NO:4: amino acid sequence of GTL1 from *Arabidopsis thaliana*
SEQ ID NO: 5: base sequence of GT2-encoding gene from *Arabidopsis thaliana*
SEQ ID NO:6: amino acid sequence of GT2 from *Arabidopsis thaliana*
SEQ ID NO:7: base sequence of cis-prenyltransferase-encoding gene from *Hevea brasiliensis*
SEQ ID NO:8: amino acid sequence of cis-prenyltransferase from *Hevea brasiliensis*
SEQ ID NO:9: base sequence of HMG-CoA reductase-encoding gene from *Hevea brasiliensis*
SEQ ID NO:10: amino acid sequence of HMG-CoA reductase from *Hevea brasiliensis*
SEQ ID NO:11: base sequence of IPP isomerase-encoding gene from *Hevea brasiliensis*
SEQ ID NO:12: amino acid sequence of IPP isomerase from *Hevea brasiliensis*
SEQ ID NO:13: base sequence of SRPP-encoding gene from *Hevea brasiliensis*
SEQ ID NO:14: amino acid sequence of SRPP from *Hevea brasiliensis*
SEQ ID NO:15: Primer 1
SEQ ID NO:16: Primer 2
SEQ ID NO:17: Primer 3
SEQ ID NO:18: Primer 4
SEQ ID NO:19: Primer 5
SEQ ID NO:20: Primer 6
SEQ ID NO:21: base sequence of promoter sequence of HMG-CoA reductase from *Hevea brasiliensis*
SEQ ID NO:22: base sequence of promoter sequence of IPP isomerase from *Hevea brasiliensis*
SEQ ID NO:23: base sequence of promoter sequence of cis-prenyltransferase from *Hevea brasiliensis*
SEQ ID NO:24: base sequence of promoter sequence of SRPP from *Hevea brasiliensis*

The invention claimed is:

1. An isoprenoid-producing plant, into which a heterologous gene encoding a light-responsive transcription factor has been introduced,
   wherein the gene is either of the following DNAs:
   [1] a DNA comprising the sequence of SEQ ID NO:1; and
   [2] a DNA encoding a protein with light-responsive transcription factor activity, and having a sequence that has at least 90% sequence identity to the sequence of SEQ ID NO:1,
   wherein the isoprenoid-producing plant is selected from the group consisting of plants of the genus *Hevea*.

2. A method for producing polyisoprenoids growing the isoprenoid-producing plant according to claim 1.

* * * * *

```
                         SEQUENCE LISTING

<160> NUMBER OF SEQ ID NOS: 24

<210> SEQ ID NO 1
<211> LENGTH: 1221
<212> TYPE: DNA
<213> ORGANISM: Arabidopsis thaliana

<400> SEQUENCE: 1
atgttcattt ccgacaaatc tcgtcctact gatttctaca aagacgatca tcacaattcc      60
tccaccacca gcaccacacg cgatatgatg atcgatgtac tcaccactac caacgaatca     120
gtagatctac aatctcacca ccaccacaat caccacaatc atcatctcca ccaatctcag     180
ccacaacaac agattctcct cggagaaagc agtggagaag atcacgaagt taaagcacca     240
aagaaacgag cggagacatg ggttcaagac gaaactcgta gcttaatcat gttccgtaga     300
ggtatggatg gtttattcaa tacatccaaa tctaataaac atctctggga acagatttcg     360
tctaagatga gagaaaaagg gtttgatcga tctccgacta tgtgtactga taatggagg     420 aatctgttga aagagtttaa gaaagctaag catcatgata gaggaaatgg atcggcgaag     480
atgtcgtatt acaaagagat tgaagatatt cttagagaga ggagcaaaaa agtgacacca     540
ccacagtata ataagagccc taatacacca cctacatcag ccaaagttga ttcctttatg     600
caatttactg ataaaggttt tgatgatacg agcatttctt ttggatccgt tgaagctaat     660
ggcaggccag ccttaaacct tgaaaggcgt cttgatcatg atggtcatcc tcttgcaatc     720
actacagcag ttgatgctgt tgcagcaaat ggagttactc cttggaattg agagagact     780 cctggaaacg gtgatgatag tcatggtcag cctttttggtg gtagggtcat aacagtgaaa     840
tttggtgact atacaagaag aatcggtgtt gatggtagtc agaagcaat caaagaggta      900 atcagatctg cttttgggtt aagaactcga agggcttttt ggttagaaga tgaagatcag     960
attattcgct gtcttgaccg agacatgccc ttagggaact atctactccg tctggatgat    1020
ggactggcca ttagggtttg ccattatgat gaatccaacc aattaccagt ccattcgaa     1080 gagaaaatct tctacactga agaagactac cgcgagtttc tggctctaca gggatggtca    1140
```

```
agcctgcaag ttgatggttt taggaacata gaaaacatgg atgatcttca acctggtgct   1200
gtgtatcgag gtgtgagatg a                                              1221
```

<210> SEQ ID NO 2
<211> LENGTH: 406
<212> TYPE: PRT
<213> ORGANISM: Arabidopsis thaliana

<400> SEQUENCE: 2

| | | | | | | | | | | | | | | |
|---|---|---|---|---|---|---|---|---|---|---|---|---|---|---|
| Met | Phe | Ile | Ser | Asp | Lys | Ser | Arg | Pro | Thr | Asp | Phe | Tyr | Lys | Asp Asp |
| 1 | | | | 5 | | | | | 10 | | | | | 15 |
| His | His | Asn | Ser | Ser | Thr | Thr | Ser | Thr | Thr | Arg | Asp | Met | Met | Ile Asp |
| | | | 20 | | | | | 25 | | | | | 30 | |
| Val | Leu | Thr | Thr | Thr | Asn | Glu | Ser | Val | Asp | Leu | Gln | Ser | His | His His |
| | | | 35 | | | | | 40 | | | | | 45 | |
| His | Asn | His | His | Asn | His | His | Leu | His | Gln | Ser | Gln | Pro | Gln | Gln Gln |
| | | | 50 | | | | | 55 | | | | | 60 | |
| Ile | Leu | Leu | Gly | Glu | Ser | Ser | Gly | Glu | Asp | His | Glu | Val | Lys | Ala Pro |
| 65 | | | | | 70 | | | | | 75 | | | | | 80 |
| Lys | Lys | Arg | Ala | Glu | Thr | Trp | Val | Gln | Asp | Glu | Thr | Arg | Ser | Leu Ile |
| | | | | 85 | | | | | 90 | | | | | 95 | |
| Met | Phe | Arg | Arg | Gly | Met | Asp | Gly | Leu | Phe | Asn | Thr | Ser | Lys | Ser Asn |
| | | | 100 | | | | | 105 | | | | | 110 | | |
| Lys | His | Leu | Trp | Glu | Gln | Ile | Ser | Ser | Lys | Met | Arg | Glu | Lys | Gly Phe |
| | | | 115 | | | | | 120 | | | | | 125 | | |
| Asp | Arg | Ser | Pro | Thr | Met | Cys | Thr | Asp | Lys | Trp | Arg | Asn | Leu | Leu Lys |
| | | | 130 | | | | | 135 | | | | | 140 | | |
| Glu | Phe | Lys | Lys | Ala | Lys | His | His | Asp | Arg | Gly | Asn | Gly | Ser | Ala Lys |
| 145 | | | | | 150 | | | | | 155 | | | | | 160 |
| Met | Ser | Tyr | Tyr | Lys | Glu | Ile | Glu | Asp | Ile | Leu | Arg | Glu | Arg | Ser Lys |
| | | | | 165 | | | | | 170 | | | | | 175 | |
| Lys | Val | Thr | Pro | Pro | Gln | Tyr | Asn | Lys | Ser | Pro | Asn | Thr | Pro | Pro Thr |
| | | | 180 | | | | | 185 | | | | | 190 | | |
| Ser | Ala | Lys | Val | Asp | Ser | Phe | Met | Gln | Phe | Thr | Asp | Lys | Gly | Phe Asp |
| | | | 195 | | | | | 200 | | | | | 205 | | |
| Asp | Thr | Ser | Ile | Ser | Phe | Gly | Ser | Val | Glu | Ala | Asn | Gly | Arg | Pro Ala |
| | | | 210 | | | | | 215 | | | | | 220 | | |
| Leu | Asn | Leu | Glu | Arg | Arg | Leu | Asp | His | Asp | Gly | His | Pro | Leu | Ala Ile |
| 225 | | | | | 230 | | | | | 235 | | | | | 240 |
| Thr | Thr | Ala | Val | Asp | Ala | Val | Ala | Ala | Asn | Gly | Val | Thr | Pro | Trp Asn |
| | | | | 245 | | | | | 250 | | | | | 255 | |
| Trp | Arg | Glu | Thr | Pro | Gly | Asn | Gly | Asp | Asp | Ser | His | Gly | Gln | Pro Phe |
| | | | 260 | | | | | 265 | | | | | 270 | | |
| Gly | Gly | Arg | Val | Ile | Thr | Val | Lys | Phe | Gly | Asp | Tyr | Thr | Arg | Arg Ile |
| | | | 275 | | | | | 280 | | | | | 285 | | |
| Gly | Val | Asp | Gly | Ser | Ala | Glu | Ala | Ile | Lys | Glu | Val | Ile | Arg | Ser Ala |
| | | | 290 | | | | | 295 | | | | | 300 | | |
| Phe | Gly | Leu | Arg | Thr | Arg | Arg | Ala | Phe | Trp | Leu | Glu | Asp | Glu | Asp Gln |
| 305 | | | | | 310 | | | | | 315 | | | | | 320 |
| Ile | Ile | Arg | Cys | Leu | Asp | Arg | Asp | Met | Pro | Leu | Gly | Asn | Tyr | Leu Leu |
| | | | | 325 | | | | | 330 | | | | | 335 | |
| Arg | Leu | Asp | Asp | Gly | Leu | Ala | Ile | Arg | Val | Cys | His | Tyr | Asp | Glu Ser |
| | | | 340 | | | | | 345 | | | | | 350 | | |

```
Asn Gln Leu Pro Val His Ser Glu Glu Lys Ile Phe Tyr Thr Glu Glu
            355                 360                 365

Asp Tyr Arg Glu Phe Leu Ala Leu Gln Gly Trp Ser Ser Leu Gln Val
370                 375                 380

Asp Gly Phe Arg Asn Ile Glu Asn Met Asp Asp Leu Gln Pro Gly Ala
385                 390                 395                 400

Val Tyr Arg Gly Val Arg
                405

<210> SEQ ID NO 3
<211> LENGTH: 2010
<212> TYPE: DNA
<213> ORGANISM: Arabidopsis thaliana

<400> SEQUENCE: 3
atggagcaag gaggaggtgg tggtggtaat gaagttgtgg aggaagcttc acctattagt        60
tcaagacctc ctgctaacaa cttagaagag cttatgagat ctcagccgc cgcggatgac       120 ggtggattag gaggtggagg tggaggagga ggaggaggaa gtgcttcttc ttcatcggga       180
aatcgatggc cgagagaaga aactttagct cttcttcgga tccgatccga tatggattct       240
acttttcgtg atgctactct caaagctcct ctttgggaac atgtttccag gaagctattg       300
gagttaggtt acaaacgaag ttcaaagaaa tgcaaagaga aattcgaaaa cgttcagaaa       360
tattacaaac gtactaaaga aactcgcggt ggtcgtcatg atggtaaagc ttacaagttc       420
ttctctcagc ttgaagctct caacactact cctccttcat cttccctcga cgttactcct       480
ctctccgtcg ctaatcccat tctcatgcct tcttcttctt cttctccatt tcccgtattc       540
tctcaaccgc aaccgcaaac gcaaacgcaa ccgcctcaaa cgcataatgt ctcttttact       600
cctactccac cacctcttcc acttccttca atgggtccga tatttaccgg tgttactttc       660
tcgtctcata gctcatcgac ggcttcagga atggggtctg atgatgatga cgacgatatg       720
gacgttgatc aggctaacat tgcgggttct agtagccgaa aacgcaaacg tggaaaccgc       780
ggtggaggcg gtaaaatgat ggaattgttt gaaggtttgg tgagacaagt aatgcaaaag       840
caagcggcta tgcaaaggag tttcttggaa gctcttgaga agagagagca agaacgtctt       900
gatcgtgaag aagcttggaa cgtcaagaa atggctcggt tagctcgaga cacgaggtc        960 atgtctcaag aacgagccgc ctctgcttct cgtgacgccg caatcatttc attgattcag      1020
aaaattactg ccataccat tcagttacct ccttcttttgt catctcaacc gcctccaccg      1080
tatcaaccgc cacccgcggt cactaaacgt gtggcggaac caccattatc aacagctcaa      1140
tctcaatcac aacaaccaat aatggcgatt ccacaacaac aaattcttcc tcctcctcct      1200
ccttctcatc ctcacgctca tcaaccagaa cagaaacaac aacaacaacc acaacaagag      1260
atggtcatga gctcggaaca atcatcatta ccatcatcat caagatggcc aaaggcagag      1320
attctagcgc ttataaacct gagaagtgga atggaaccaa ggtaccaaga taatgtacct      1380
aaaggacttc tatgggaaga gatctcaact tcaatgaaga gaatgggata caacagaaac      1440
gctaagagat gtaaagagaa atgggaaaac ataaacaaat actacaagaa agttaaagaa      1500
agcaacaaga aacgtcctca agatgctaag acttgtcctt actttcaccg cctcgatctt      1560
ctttaccgca caaagtact cggtagtggc ggtggttcta gcacttctgg tctacctcaa      1620
gaccaaaaac agagtccggt cactgcgatg aaaccgccac aagaaggact tgttaatgtt      1680
caacaaactc atgggtcagc ttcaactgag gaagaagagc ctatagagga aagtccacaa      1740
ggaacagaaa agccagaaga ccttgtgatg agagagctga ttcaacaaca acagcaacta      1800
```

```
caacaacaag aatcaatgat aggtgagtat gaaaagattg aagagtctca caattataat   1860
aacatggagg aagaggaaga tcaggaaatg gatgaggaag aactagacga ggatgagaag   1920
tccgcggctt tcgagattgc gtttcaaagc cctgcaaaca gaggaggcaa tggccatacg   1980
gaaccacctt tcttgacaat ggttcagtaa                                    2010

<210> SEQ ID NO 4
<211> LENGTH: 669
<212> TYPE: PRT
<213> ORGANISM: Arabidopsis thaliana

<400> SEQUENCE: 4
```

Met Glu Gln Gly Gly Gly Gly Gly Asn Glu Val Val Glu Glu Ala
1               5                   10                  15

Ser Pro Ile Ser Ser Arg Pro Ala Asn Asn Leu Glu Glu Leu Met
                20                  25                  30

Arg Phe Ser Ala Ala Ala Asp Asp Gly Gly Leu Gly Gly Gly Gly
            35                  40                  45

Gly Gly Gly Gly Gly Ser Ala Ser Ser Ser Gly Asn Arg Trp Pro
        50                  55                  60

Arg Glu Glu Thr Leu Ala Leu Leu Arg Ile Arg Ser Asp Met Asp Ser
65                  70                  75                  80

Thr Phe Arg Asp Ala Thr Leu Lys Ala Pro Leu Trp Glu His Val Ser
                85                  90                  95

Arg Lys Leu Leu Glu Leu Gly Tyr Lys Arg Ser Ser Lys Lys Cys Lys
            100                 105                 110

Glu Lys Phe Glu Asn Val Gln Lys Tyr Tyr Lys Arg Thr Lys Glu Thr
        115                 120                 125

Arg Gly Gly Arg His Asp Gly Lys Ala Tyr Lys Phe Phe Ser Gln Leu
    130                 135                 140

Glu Ala Leu Asn Thr Thr Pro Pro Ser Ser Leu Asp Val Thr Pro
145                 150                 155                 160

Leu Ser Val Ala Asn Pro Ile Leu Met Pro Ser Ser Ser Ser Pro
                165                 170                 175

Phe Pro Val Phe Ser Gln Pro Gln Pro Gln Thr Gln Thr Gln Pro Pro
            180                 185                 190

Gln Thr His Asn Val Ser Phe Thr Pro Thr Pro Pro Leu Pro Leu
        195                 200                 205

Pro Ser Met Gly Pro Ile Phe Thr Gly Val Thr Phe Ser Ser His Ser
    210                 215                 220

Ser Ser Thr Ala Ser Gly Met Gly Ser Asp Asp Asp Asp Asp Met
225                 230                 235                 240

Asp Val Asp Gln Ala Asn Ile Ala Gly Ser Ser Arg Lys Arg Lys
                245                 250                 255

Arg Gly Asn Arg Gly Gly Gly Lys Met Met Glu Leu Phe Glu Gly
            260                 265                 270

Leu Val Arg Gln Val Met Gln Lys Gln Ala Ala Met Gln Arg Ser Phe
        275                 280                 285

Leu Glu Ala Leu Glu Lys Arg Glu Gln Glu Arg Leu Asp Arg Glu Glu
    290                 295                 300

Ala Trp Lys Arg Gln Glu Met Ala Arg Leu Ala Arg Glu His Glu Val
305                 310                 315                 320

Met Ser Gln Glu Arg Ala Ala Ser Ala Ser Arg Asp Ala Ala Ile Ile
                325                 330                 335

```
Ser Leu Ile Gln Lys Ile Thr Gly His Thr Ile Gln Leu Pro Pro Ser
        340                 345                 350

Leu Ser Ser Gln Pro Pro Pro Tyr Gln Pro Pro Ala Val Thr
        355                 360                 365

Lys Arg Val Ala Glu Pro Pro Leu Ser Thr Ala Gln Ser Gln Ser Gln
370                 375                 380

Gln Pro Ile Met Ala Ile Pro Gln Gln Gln Ile Leu Pro Pro Pro
385                 390                 395                 400

Pro Ser His Pro His Ala His Gln Pro Glu Gln Lys Gln Gln Gln Gln
            405                 410                 415

Pro Gln Gln Glu Met Val Met Ser Ser Glu Gln Ser Ser Leu Pro Ser
            420                 425                 430

Ser Ser Arg Trp Pro Lys Ala Glu Ile Leu Ala Leu Ile Asn Leu Arg
        435                 440                 445

Ser Gly Met Glu Pro Arg Tyr Gln Asp Asn Val Pro Lys Gly Leu Leu
        450                 455                 460

Trp Glu Glu Ile Ser Thr Ser Met Lys Arg Met Gly Tyr Asn Arg Asn
465                 470                 475                 480

Ala Lys Arg Cys Lys Glu Lys Trp Glu Asn Ile Asn Lys Tyr Tyr Lys
            485                 490                 495

Lys Val Lys Glu Ser Asn Lys Lys Arg Pro Gln Asp Ala Lys Thr Cys
            500                 505                 510

Pro Tyr Phe His Arg Leu Asp Leu Leu Tyr Arg Asn Lys Val Leu Gly
        515                 520                 525

Ser Gly Gly Gly Ser Ser Thr Ser Gly Leu Pro Gln Asp Gln Lys Gln
        530                 535                 540

Ser Pro Val Thr Ala Met Lys Pro Pro Gln Glu Gly Leu Val Asn Val
545                 550                 555                 560

Gln Gln Thr His Gly Ser Ala Ser Thr Glu Glu Glu Pro Ile Glu
            565                 570                 575

Glu Ser Pro Gln Gly Thr Glu Lys Pro Glu Asp Leu Val Met Arg Glu
            580                 585                 590

Leu Ile Gln Gln Gln Gln Leu Gln Gln Gln Glu Ser Met Ile Gly
        595                 600                 605

Glu Tyr Glu Lys Ile Glu Glu Ser His Asn Tyr Asn Asn Met Glu Glu
        610                 615                 620

Glu Glu Asp Gln Glu Met Asp Glu Glu Leu Asp Glu Asp Glu Lys
625                 630                 635                 640

Ser Ala Ala Phe Glu Ile Ala Phe Gln Ser Pro Ala Asn Arg Gly Gly
            645                 650                 655

Asn Gly His Thr Glu Pro Pro Phe Leu Thr Met Val Gln
            660                 665
```

<210> SEQ ID NO 5
<211> LENGTH: 1728
<212> TYPE: DNA
<213> ORGANISM: Arabidopsis thaliana

<400> SEQUENCE: 5

```
atgtctggaa actcagaagg actgttagag agctcaggcg gcggcgtggg aggttccgtc      60
gaggaggaaa aagatatgaa gatggaggaa accggtgaag gagccggcag cggaggaaac     120
cggtggccaa gaccagagac tttagctcta ttgagaatac gttcagagat ggataaagct     180
tttcgtgact ctactctcaa agctccctta tgggaagaaa tttccaggaa aatgatggag     240
```

```
cttggttaca agagaagttc aaagaaatgc aaggagaagt tcgagaacgt gtacaagtac    300
cacaaacgta ccaaagaagg tcgtaccggg aaatccgaag gcaaaactta ccggtttttc    360
gaagagttag aagctttcga gactctcagt tcctatcaac ctgaacctga gtcgcaaccc    420
gcgaaatctt ctgcagtgat cacgaacgcg cccgcaacct cttccttgat accatggatt    480
agctctagca atccatcaac cgaaaaaagt tcttcaccgt tgaaacatca tcatcaggtt    540
agtgtacaac ccatcaccac aaaccctacc ttcctcgcca agcaaccatc ttccacgacg    600
ccttttcctt tttatagcag caacaatact actactgtta gccagccgcc aatttcaaat    660
gacttgatga acaatgtttc atcgctgaat cttttctcga gctcaacttc ttcatctact    720
gcatctgacg aggaagaaga tcatcatcag gttaagagct cgagaaagaa gaggaagtat    780
tggaaagggt gtttacgaa gttgacaaaa gagttaatgg agaaacaaga gaagatgcaa    840
aaaaggttct tggaaacact ggagtatcgt gagaaagaga aatctcaag agaagaagct    900
tggagggtcc aagagatagg gagaatcaac agagaacacg aaacattaat ccatgagagg    960
tccaatgctg cagctaaaga cgctgcaatc atatccttct tacacaaaat ctcaggagga   1020
caaccacaac aaccgcaaca acataatcat aaaccatcac aaaggaaaca atatcaaagc   1080
gatcattcaa taacgtttga gagtaaagag ccgagggcgg ttctattgga tacaacaata   1140
aagatgggga attacgataa caatcattcg gtgtctccta gttcttcaag atggcctaaa   1200
accgaggtcg aggccttgat aaggataaga agaatcttg aagctaacta tcaagaaaac   1260
ggtactaagg gaccattatg ggaagagatc tctgcaggga tgagaagatt gggatacaat   1320
agaagcgcga aacgctgcaa agagaagtgg gaaaacatca acaagtactt taagaaagtc   1380
aaagaaagca acaagaaacg tccccttgat tccaagactt gcccttattt tcaccagctc   1440
gaagctttgt acaacgagag gaacaaaagt ggggcaatgc cattgccatt gcctctaatg   1500
gtgactccac agagacagtt gcttctctcg caagaaaccc agaccgagtt tgagactgat   1560
cagagggaaa aagttggtga taagaagat gaagaagaag gagagagtga agaagatgaa   1620
tacgatgaag aagaagaggg agaaggagac aatgagacaa gtgagttcga gattgtgttg   1680
aacaaaacat cttcacctat ggacattaac aataatcttt tcacctaa                 1728
```

<210> SEQ ID NO 6
<211> LENGTH: 575
<212> TYPE: PRT
<213> ORGANISM: Arabidopsis thaliana

<400> SEQUENCE: 6

```
Met Ser Gly Asn Ser Glu Gly Leu Leu Glu Ser Ser Gly Gly Val
1               5                   10                  15

Gly Gly Ser Val Glu Glu Lys Asp Met Lys Met Glu Glu Thr Gly
                20                  25                  30

Glu Gly Ala Gly Ser Gly Gly Asn Arg Trp Pro Arg Pro Glu Thr Leu
            35                  40                  45

Ala Leu Leu Arg Ile Arg Ser Glu Met Asp Lys Ala Phe Arg Asp Ser
    50                  55                  60

Thr Leu Lys Ala Pro Leu Trp Glu Glu Ile Ser Arg Lys Met Met Glu
65                  70                  75                  80

Leu Gly Tyr Lys Arg Ser Ser Lys Lys Cys Lys Glu Lys Phe Glu Asn
                85                  90                  95

Val Tyr Lys Tyr His Lys Arg Thr Lys Glu Gly Arg Thr Gly Lys Ser
            100                 105                 110
```

-continued

Glu Gly Lys Thr Tyr Arg Phe Phe Glu Glu Leu Glu Ala Phe Glu Thr
            115                 120                 125
Leu Ser Ser Tyr Gln Pro Glu Pro Glu Ser Gln Pro Ala Lys Ser Ser
            130                 135                 140
Ala Val Ile Thr Asn Ala Pro Ala Thr Ser Ser Leu Ile Pro Trp Ile
145                 150                 155                 160
Ser Ser Ser Asn Pro Ser Thr Glu Lys Ser Ser Ser Pro Leu Lys His
                165                 170                 175
His His Gln Val Ser Val Gln Pro Ile Thr Thr Asn Pro Thr Phe Leu
            180                 185                 190
Ala Lys Gln Pro Ser Ser Thr Thr Pro Phe Pro Phe Tyr Ser Ser Asn
            195                 200                 205
Asn Thr Thr Thr Val Ser Gln Pro Pro Ile Ser Asn Asp Leu Met Asn
210                 215                 220
Asn Val Ser Ser Leu Asn Leu Phe Ser Ser Thr Ser Ser Ser Thr
225                 230                 235                 240
Ala Ser Asp Glu Glu Asp His His Gln Val Lys Ser Ser Arg Lys
                245                 250                 255
Lys Arg Lys Tyr Trp Lys Gly Leu Phe Thr Lys Leu Thr Lys Glu Leu
            260                 265                 270
Met Glu Lys Gln Glu Lys Met Gln Lys Arg Phe Leu Glu Thr Leu Glu
            275                 280                 285
Tyr Arg Glu Lys Glu Arg Ile Ser Arg Glu Glu Ala Trp Arg Val Gln
            290                 295                 300
Glu Ile Gly Arg Ile Asn Arg Glu His Glu Thr Leu Ile His Glu Arg
305                 310                 315                 320
Ser Asn Ala Ala Ala Lys Asp Ala Ala Ile Ile Ser Phe Leu His Lys
                325                 330                 335
Ile Ser Gly Gly Gln Pro Gln Gln Pro Gln Gln His Asn His Lys Pro
            340                 345                 350
Ser Gln Arg Lys Gln Tyr Gln Ser Asp His Ser Ile Thr Phe Glu Ser
            355                 360                 365
Lys Glu Pro Arg Ala Val Leu Leu Asp Thr Thr Ile Lys Met Gly Asn
            370                 375                 380
Tyr Asp Asn Asn His Ser Val Ser Pro Ser Ser Arg Trp Pro Lys
385                 390                 395                 400
Thr Glu Val Glu Ala Leu Ile Arg Ile Arg Lys Asn Leu Glu Ala Asn
            405                 410                 415
Tyr Gln Glu Asn Gly Thr Lys Gly Pro Leu Trp Glu Glu Ile Ser Ala
            420                 425                 430
Gly Met Arg Arg Leu Gly Tyr Asn Arg Ser Ala Lys Arg Cys Lys Glu
            435                 440                 445
Lys Trp Glu Asn Ile Asn Lys Tyr Phe Lys Lys Val Lys Glu Ser Asn
            450                 455                 460
Lys Lys Arg Pro Leu Asp Ser Lys Thr Cys Pro Tyr Phe His Gln Leu
465                 470                 475                 480
Glu Ala Leu Tyr Asn Glu Arg Asn Lys Ser Gly Ala Met Pro Leu Pro
                485                 490                 495
Leu Pro Leu Met Val Thr Pro Gln Arg Gln Leu Leu Leu Ser Gln Glu
            500                 505                 510
Thr Gln Thr Glu Phe Glu Thr Asp Gln Arg Glu Lys Val Gly Asp Lys
            515                 520                 525

Glu Asp Glu Glu Gly Glu Ser Glu Asp Glu Tyr Asp Glu
    530             535             540

Glu Glu Gly Glu Gly Asp Asn Glu Thr Ser Glu Phe Glu Ile Val Leu
545             550             555             560

Asn Lys Thr Ser Ser Pro Met Asp Ile Asn Asn Asn Leu Phe Thr
                565             570             575

<210> SEQ ID NO 7
<211> LENGTH: 873
<212> TYPE: DNA
<213> ORGANISM: Hevea brasiliensis

<400> SEQUENCE: 7

```
atgaaattat acaccggtga gaggccaagt gtgttcagac ttttagggaa gtatatgaga    60
aaagggttat atggcatcct aacccagggt cccatcccta ctcatcttgc cttcatattg   120
gatggaaaca ggaggtttgc taagaagcat aaactgccag aaggaggtgg tcataaggct   180
ggatttttag ctcttctgaa cgtgctaact tattgctatg agttaggagt gaaatatgcg   240
actatctatg cctttagcat cgataatttt cgaaggaaac ctcatgaggt tcagtacgta   300
atgaatctaa tgctggagaa gattgaaggg atgatcatgg aagaaagtat catcaatgca   360
tatgatattt gcgtacgttt tgtgggtaac ctgaagcttt taagtgagcc agtcaagacc   420
gcagcagata agattatgag ggctactgcc aacaattcca aatgtgtgct ctctccttgct  480
gtatgctata cttcaactga tgagatcgtg catgctgttg aagaatcctc tgaattgaac   540
tccaatgaag tttgtaacaa tcaagaattg gaggaggcaa atgcaactgg aagcggtact   600
gtgattcaaa ctgagaacat ggagtcgtat tctggaataa aacttgtaga ccttgagaaa   660
aacacctaca taaatcctta tcctgatgtt ctgattcgaa cttctgggga gacccgtctg   720
agcaactact tactttggca gactactaat tgcatactgt attctcctta tgcactgtgg   780
ccagagattg tcttcgaca cgtggtgtgg tcagtaatta acttccaacg tcattattct   840
tacttggaga aacataagga atacttaaaa taa                                873
```

<210> SEQ ID NO 8
<211> LENGTH: 290
<212> TYPE: PRT
<213> ORGANISM: Hevea brasiliensis

<400> SEQUENCE: 8

Met Lys Leu Tyr Thr Gly Glu Arg Pro Ser Val Phe Arg Leu Leu Gly
1               5                   10                  15

Lys Tyr Met Arg Lys Gly Leu Tyr Gly Ile Leu Thr Gln Gly Pro Ile
            20                  25                  30

Pro Thr His Leu Ala Phe Ile Leu Asp Gly Asn Arg Arg Phe Ala Lys
        35                  40                  45

Lys His Lys Leu Pro Glu Gly Gly Gly His Lys Ala Gly Phe Leu Ala
    50                  55                  60

Leu Leu Asn Val Leu Thr Tyr Cys Tyr Glu Leu Gly Val Lys Tyr Ala
65                  70                  75                  80

Thr Ile Tyr Ala Phe Ser Ile Asp Asn Phe Arg Arg Lys Pro His Glu
                85                  90                  95

Val Gln Tyr Val Met Asn Leu Met Leu Glu Lys Ile Glu Gly Met Ile
            100                 105                 110

Met Glu Glu Ser Ile Ile Asn Ala Tyr Asp Ile Cys Val Arg Phe Val
        115                 120                 125

```
Gly Asn Leu Lys Leu Leu Ser Glu Pro Val Lys Thr Ala Ala Asp Lys
    130                 135                 140

Ile Met Arg Ala Thr Ala Asn Asn Ser Lys Cys Val Leu Leu Leu Ala
145                 150                 155                 160

Val Cys Tyr Thr Ser Thr Asp Glu Ile Val His Ala Val Glu Ser
                165                 170                 175

Ser Glu Leu Asn Ser Asn Glu Val Cys Asn Asn Gln Glu Leu Glu Glu
                180                 185                 190

Ala Asn Ala Thr Gly Ser Gly Thr Val Ile Gln Thr Glu Asn Met Glu
                195                 200                 205

Ser Tyr Ser Gly Ile Lys Leu Val Asp Leu Glu Lys Asn Thr Tyr Ile
210                 215                 220

Asn Pro Tyr Pro Asp Val Leu Ile Arg Thr Ser Gly Glu Thr Arg Leu
225                 230                 235                 240

Ser Asn Tyr Leu Leu Trp Gln Thr Thr Asn Cys Ile Leu Tyr Ser Pro
                245                 250                 255

Tyr Ala Leu Trp Pro Glu Ile Gly Leu Arg His Val Val Trp Ser Val
                260                 265                 270

Ile Asn Phe Gln Arg His Tyr Ser Tyr Leu Glu Lys His Lys Glu Tyr
                275                 280                 285

Leu Lys
    290

<210> SEQ ID NO 9
<211> LENGTH: 1728
<212> TYPE: DNA
<213> ORGANISM: Hevea brasiliensis

<400> SEQUENCE: 9
atggacacca ccggccggct ccaccaccga aagcatgcta cacccgttga ggaccgttct      60
ccgaccactc cgaaagcgtc ggacgcgctt ccgcttcccc tctacctgac caacgcggtt     120
ttcttcacgc tgttcttctc ggtggcgtat tacctccttc accggtggcg cgacaagatc     180
cgcaactcca ctcccttca tatcgttact ctctctgaaa ttgttgctat tgtctccctc     240
attgcctctt tcatttacct cctaggattc ttcggtatcg attttgtgca gtcattcatt     300
gcacgcgcct cccatgacgt gtgggacctc gaagatacgg atcccaacta cctcatcgat     360
gaagatcacc gtctcgttac ttgccctccc gctaatatat ctactaagac taccattatt     420
gccgcaccta ccaaattgcc tacctcggaa cccttaattg caccctagt ctcggaggaa     480 gacgaaatga tcgtcaactc cgtcgtggat gggaagatac cctcctattc tctggagtcg     540
aagctcgggg actgcaaacg agcggctgcg attcgacgcg aggctttgca gaggatgaca     600
aggaggtcgc tggaaggctt gccagtagaa gggttcgatt acgagtcgat tttaggacaa     660
tgctgtgaaa tgccagtggg atacgtgcag attccggtgg ggattgcggg gccgttgttg     720
ctgaacgggc gggagtactc tgttccaatg gcgaccacgg agggttgttt ggtgcgagc     780 actaatagag ggtgtaaggc gatttacttg tcaggtgggg ccaccagcgt cttgttgaag     840
gatggcatga caagagcgcc tgttgtaaga ttcgcgtcgg cgactagagc cgcggagttg     900
aagttcttct tggaggatcc tgacaatttt gataccttgg ccgtagtttt taacaagtcc     960
agtagatttg cgaggctcca aggcattaaa tgctcaattg ctggtaagaa tctttatata    1020
agattcagct gcagcactgg cgatgcaatg ggatgaaca tggttctaa aggggttcaa    1080 aacgttcttg aatttcttca aagtgatttt tctgatatgg atgtcattgg aatctcagga    1140
```

-continued

```
aattttttgtt cggataagaa gcctgctgct gtaaattgga ttgaaggacg tggcaaatca      1200
gttgtttgtg aggcaattat caaggaagag gtggtgaaga aggtgttgaa aaccaatgtg      1260
gcctccctag tggagcttaa catgctcaag aatcttgctg gttctgctgt tgctggtgct      1320
ttgggtggat ttaatgccca tgcaggcaac atcgtatctg caatctttat tgccactggc      1380
caggatccag cacagaatgt tgagagttct cattgcatta ccatgatgga agctgtcaat      1440
gatgaaaggg atctccatat ctctgtgacc atgccctcca ttgaggtggg tacagtcgga      1500
ggtggaactc aacttgcatc tcagtctgct tgtctcaatt tgcttggggt gaagggtgca      1560
aacaaagagt cgccaggatc aaactcaagg ctccttgctg ccatcgtagc tggttcagtt      1620
ttggctggtg agctctcctt gatgtctgcc attgcagctg ggcagcttgt caagagtcac      1680
atgaagtaca acagctccag caaagatatg tctaaagctg catcttag                   1728
```

<210> SEQ ID NO 10
<211> LENGTH: 575
<212> TYPE: PRT
<213> ORGANISM: Hevea brasiliensis

<400> SEQUENCE: 10

```
Met Asp Thr Thr Gly Arg Leu His His Arg Lys His Ala Thr Pro Val
1               5                   10                  15

Glu Asp Arg Ser Pro Thr Thr Pro Lys Ala Ser Asp Ala Leu Pro Leu
            20                  25                  30

Pro Leu Tyr Leu Thr Asn Ala Val Phe Phe Thr Leu Phe Phe Ser Val
        35                  40                  45

Ala Tyr Tyr Leu Leu His Arg Trp Arg Asp Lys Ile Arg Asn Ser Thr
    50                  55                  60

Pro Leu His Ile Val Thr Leu Ser Glu Ile Val Ala Ile Val Ser Leu
65                  70                  75                  80

Ile Ala Ser Phe Ile Tyr Leu Leu Gly Phe Phe Gly Ile Asp Phe Val
                85                  90                  95

Gln Ser Phe Ile Ala Arg Ala Ser His Asp Val Trp Asp Leu Glu Asp
            100                 105                 110

Thr Asp Pro Asn Tyr Leu Ile Asp Glu Asp His Arg Leu Val Thr Cys
        115                 120                 125

Pro Pro Ala Asn Ile Ser Thr Lys Thr Thr Ile Ala Ala Pro Thr
    130                 135                 140

Lys Leu Pro Thr Ser Glu Pro Leu Ile Ala Pro Leu Val Ser Glu Glu
145                 150                 155                 160

Asp Glu Met Ile Val Asn Ser Val Val Asp Gly Lys Ile Pro Ser Tyr
                165                 170                 175

Ser Leu Glu Ser Lys Leu Gly Asp Cys Lys Arg Ala Ala Ala Ile Arg
            180                 185                 190

Arg Glu Ala Leu Gln Arg Met Thr Arg Arg Ser Leu Glu Gly Leu Pro
        195                 200                 205

Val Glu Gly Phe Asp Tyr Glu Ser Ile Leu Gly Gln Cys Cys Glu Met
    210                 215                 220

Pro Val Gly Tyr Val Gln Ile Pro Val Gly Ile Ala Gly Pro Leu Leu
225                 230                 235                 240

Leu Asn Gly Arg Glu Tyr Ser Val Pro Met Ala Thr Thr Glu Gly Cys
                245                 250                 255

Leu Val Ala Ser Thr Asn Arg Gly Cys Lys Ala Ile Tyr Leu Ser Gly
            260                 265                 270
```

```
Gly Ala Thr Ser Val Leu Leu Lys Asp Gly Met Thr Arg Ala Pro Val
            275                 280                 285
Val Arg Phe Ala Ser Ala Thr Arg Ala Ala Glu Leu Lys Phe Phe Leu
            290                 295                 300
Glu Asp Pro Asp Asn Phe Asp Thr Leu Ala Val Val Phe Asn Lys Ser
305                 310                 315                 320
Ser Arg Phe Ala Arg Leu Gln Gly Ile Lys Cys Ser Ile Ala Gly Lys
                325                 330                 335
Asn Leu Tyr Ile Arg Phe Ser Tyr Ser Thr Gly Asp Ala Met Gly Met
            340                 345                 350
Asn Met Val Ser Lys Gly Val Gln Asn Val Leu Glu Phe Leu Gln Ser
            355                 360                 365
Asp Phe Ser Asp Met Asp Val Ile Gly Ile Ser Gly Asn Phe Cys Ser
370                 375                 380
Asp Lys Lys Pro Ala Ala Val Asn Trp Ile Glu Gly Arg Gly Lys Ser
385                 390                 395                 400
Val Val Cys Glu Ala Ile Ile Lys Glu Glu Val Val Lys Lys Val Leu
                405                 410                 415
Lys Thr Asn Val Ala Ser Leu Val Glu Leu Asn Met Leu Lys Asn Leu
            420                 425                 430
Ala Gly Ser Ala Val Ala Gly Ala Leu Gly Gly Phe Asn Ala His Ala
            435                 440                 445
Gly Asn Ile Val Ser Ala Ile Phe Ile Ala Thr Gly Gln Asp Pro Ala
            450                 455                 460
Gln Asn Val Glu Ser Ser His Cys Ile Thr Met Met Glu Ala Val Asn
465                 470                 475                 480
Asp Gly Lys Asp Leu His Ile Ser Val Thr Met Pro Ser Ile Glu Val
                485                 490                 495
Gly Thr Val Gly Gly Gly Thr Gln Leu Ala Ser Gln Ser Ala Cys Leu
            500                 505                 510
Asn Leu Leu Gly Val Lys Gly Ala Asn Lys Glu Ser Pro Gly Ser Asn
            515                 520                 525
Ser Arg Leu Leu Ala Ala Ile Val Ala Gly Ser Val Leu Ala Gly Glu
530                 535                 540
Leu Ser Leu Met Ser Ala Ile Ala Ala Gly Gln Leu Val Lys Ser His
545                 550                 555                 560
Met Lys Tyr Asn Arg Ser Ser Lys Asp Met Ser Lys Ala Ala Ser
                565                 570                 575

<210> SEQ ID NO 11
<211> LENGTH: 705
<212> TYPE: DNA
<213> ORGANISM: Hevea brasiliensis

<400> SEQUENCE: 11
atgggtgagg ctccagatgt cggcatggat gctgtccaga acgcctcat gttcgacgat      60 gaatgcattt tagtagatga gaacgatggt gttgttggtc atgcttccaa atataattgt     120
catttgtggg aaaatatttt gaaggggaac gcattacata gagcttttag cgtatttctc     180
ttcaactcaa aatatgagct actccttcag caacgctctg ggacaaaggt gacattcccg     240
cttgtatgga caaacacttg ctgtagtcat cctctgtacc gtgaatctga gcttattgat     300
gaggatgctc ttggtgtgag aaatgctgca caaggaagc ttttcgatga gcttggtatc     360
cctgctgaag atgttccagt tgatcagttt actccactag gacgtatact atataaggcg     420
```

```
tcctccgatg gaaagtgggg agagcatgaa cttgattatc tgctctttat agtccgtgat    480
gttaatgtaa atccaaaccc tgatgaggta gctgatgtaa agtatgttaa ccgggatcag    540
ttgaaggagc tcttgaggaa ggcggattct ggcgaggaag gtataaattt gtcaccttgg    600
tttagactag ttgtggacaa cttcttgttg aaatggtggg aaaatgtcga aatgggaca    660 ctcaaggaag cagttgacat gaaaacgatt cacaagttga gttga                   705
```

<210> SEQ ID NO 12
<211> LENGTH: 234
<212> TYPE: PRT
<213> ORGANISM: Hevea brasiliensis

<400> SEQUENCE: 12

```
Met Gly Glu Ala Pro Asp Val Gly Met Asp Ala Val Gln Lys Arg Leu
1               5                   10                  15

Met Phe Asp Asp Glu Cys Ile Leu Val Asp Glu Asn Asp Gly Val Val
            20                  25                  30

Gly His Ala Ser Lys Tyr Asn Cys His Leu Trp Glu Asn Ile Leu Lys
        35                  40                  45

Gly Asn Ala Leu His Arg Ala Phe Ser Val Phe Leu Phe Asn Ser Lys
    50                  55                  60

Tyr Glu Leu Leu Leu Gln Gln Arg Ser Gly Thr Lys Val Thr Phe Pro
65                  70                  75                  80

Leu Val Trp Thr Asn Thr Cys Cys Ser His Pro Leu Tyr Arg Glu Ser
                85                  90                  95

Glu Leu Ile Asp Glu Asp Ala Leu Gly Val Arg Asn Ala Ala Gln Arg
            100                 105                 110

Lys Leu Phe Asp Glu Leu Gly Ile Pro Ala Glu Asp Val Pro Val Asp
        115                 120                 125

Gln Phe Thr Pro Leu Gly Arg Ile Leu Tyr Lys Ala Ser Ser Asp Gly
    130                 135                 140

Lys Trp Gly Glu His Glu Leu Asp Tyr Leu Leu Phe Ile Val Arg Asp
145                 150                 155                 160

Val Asn Val Asn Pro Asn Pro Asp Glu Val Ala Asp Val Lys Tyr Val
                165                 170                 175

Asn Arg Asp Gln Leu Lys Glu Leu Leu Arg Lys Ala Asp Ser Gly Glu
            180                 185                 190

Glu Gly Ile Asn Leu Ser Pro Trp Phe Arg Leu Val Val Asp Asn Phe
        195                 200                 205

Leu Leu Lys Trp Trp Glu Asn Val Glu Asn Gly Thr Leu Lys Glu Ala
    210                 215                 220

Val Asp Met Lys Thr Ile His Lys Leu Ser
225                 230
```

<210> SEQ ID NO 13
<211> LENGTH: 615
<212> TYPE: DNA
<213> ORGANISM: Hevea brasiliensis

<400> SEQUENCE: 13

```
atggctgaag aggtggagga agagaggcta aagtatttgg attttgtgcg agcggctgga    60
gtttatgctg tagattcttt ctcaactctc tacctttatg ccaaggacat atctggtcca   120
ttaaaacctg gtgtcgatac tattgagaat gtggtgaaga ccgtggttac tcctgtttat   180
tatattcccc ttgaggctgt caagtttgta gacaaaacgg tggatgtatc ggtcactagc   240
```

| | | |
|---|---|---|
| ctagatggcg ttgttccccc agttatcaag caggtgtctg cccaaactta ctcggtagct | 300 | |
| caagatgctc caagaattgt tcttgatgtg gcttcttcag ttttcaacac tggtgtgcag | 360 | |
| gaaggcgcaa aagctctgta cgctaatctt gaaccaaaag ctgagcaata tgcggtcatt | 420 | |
| acctggcgtg ccctcaataa gctgccacta gttcctcaag tggcaaatgt agttgtgcca | 480 | |
| accgctgttt atttctctga aaagtacaac gatgttgttc gtggcactac tgagcaggga | 540 | |
| tatagagtgt cctcttattt gcctttgttg cccactgaga aaattactaa ggtgtttgga | 600 | |
| gatgaggcat cataa | 615 | |

<210> SEQ ID NO 14
<211> LENGTH: 204
<212> TYPE: PRT
<213> ORGANISM: Hevea brasiliensis

<400> SEQUENCE: 14

Met Ala Glu Glu Val Glu Glu Arg Leu Lys Tyr Leu Asp Phe Val
1               5                   10                  15

Arg Ala Ala Gly Val Tyr Ala Val Asp Ser Phe Ser Thr Leu Tyr Leu
            20                  25                  30

Tyr Ala Lys Asp Ile Ser Gly Pro Leu Lys Pro Gly Val Asp Thr Ile
        35                  40                  45

Glu Asn Val Val Lys Thr Val Val Thr Pro Val Tyr Tyr Ile Pro Leu
    50                  55                  60

Glu Ala Val Lys Phe Val Asp Lys Thr Val Asp Val Ser Val Thr Ser
65                  70                  75                  80

Leu Asp Gly Val Val Pro Pro Val Ile Lys Gln Val Ser Ala Gln Thr
                85                  90                  95

Tyr Ser Val Ala Gln Asp Ala Pro Arg Ile Val Leu Asp Val Ala Ser
            100                 105                 110

Ser Val Phe Asn Thr Gly Val Gln Glu Gly Ala Lys Ala Leu Tyr Ala
        115                 120                 125

Asn Leu Glu Pro Lys Ala Glu Gln Tyr Ala Val Ile Thr Trp Arg Ala
    130                 135                 140

Leu Asn Lys Leu Pro Leu Val Pro Gln Val Ala Asn Val Val Val Pro
145                 150                 155                 160

Thr Ala Val Tyr Phe Ser Glu Lys Tyr Asn Asp Val Val Arg Gly Thr
                165                 170                 175

Thr Glu Gln Gly Tyr Arg Val Ser Ser Tyr Leu Pro Leu Leu Pro Thr
            180                 185                 190

Glu Lys Ile Thr Lys Val Phe Gly Asp Glu Ala Ser
        195                 200

<210> SEQ ID NO 15
<211> LENGTH: 15
<212> TYPE: DNA
<213> ORGANISM: Artificial Sequnece
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or t

<400> SEQUENCE: 15
ntcgastwts gwgtt                                                15

<210> SEQ ID NO 16

```
<211> LENGTH: 16
<212> TYPE: DNA
<213> ORGANISM: Artificial Sequnece
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 16
ngtcgtswga nawgaa                                                            16

<210> SEQ ID NO 17
<211> LENGTH: 15
<212> TYPE: DNA
<213> ORGANISM: Artificial Sequnece
<220> FEATURE:
<223> OTHER INFORMATION: Synthetic primer
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 17
wgtgnagwan canag                                                             15

<210> SEQ ID NO 18
<211> LENGTH: 15
<212> TYPE: DNA
<213> ORGANISM: Artificial Sequnece
<220> FEATURE:
<223> OTHER INFORMATION: Synthetic primer
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 18
sttntastnc tntgc                                                             15

<210> SEQ ID NO 19
<211> LENGTH: 17
<212> TYPE: DNA
<213> ORGANISM: Artificial Sequnece
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: n is a, c, g, or t

<400> SEQUENCE: 19
```

-continued

```
sstggstana twatwct                                             17

<210> SEQ ID NO 20
<211> LENGTH: 16
<212> TYPE: DNA
<213> ORGANISM: Artificial Sequnece
<220> FEATURE:
<223> OTHER INFORMATION: Synthetic primer
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 20
agwgnagwan canaga                                              16

<210> SEQ ID NO 21
<211> LENGTH: 1565
<212> TYPE: DNA
<213> ORGANISM: Hevea brasiliensis

<400> SEQUENCE: 21
ctctgcttcg cacgagtagc gttctaaatc taccaaggat gattacgaaa ggggaagcaa      60
tccttccagg aatcaaaaaa agggacatgc caatgaatgc tcgttttatt accctacaag    120
tacagtgcaa ggttgggtca gtgaatagag ttattggcac agccatgttt cctgtttcta    180
attcttggga ggttatacac aagtgaattt tgagttacag gctgagggat gaaaagaatg    240
gaattgttac actgtatttg gtagggagaa aagtaagaga ggaaagaaaa tataaagaaa    300
aaataagttt atttttattt gttttgttta aattgaataa aaaataaaga agcgtaaaaa    360
tattaaaagg aaaataaaaa tattttatct tttttttctt ttctctttaa aatagagaaa    420
aatgagagga aaatatttaa aagtataaat ataactctat atttaataat tttttttaaa    480
atttaaaaat aaaattataa ttttattatt cataaaataa tttttttctca aatattttc    540 tctttcaatc cagataaaaa gaaaaaaaat aattttatt ttcattcttt attttctctc     600
ttttaatttt ctttctccct gaaatattcc caaacacagt gttaatgttt ttgtaaaaag    660
gggcaagcag tagcagatca cgtgagaaag aatttgccta tagtattgcc cgtgttcttc    720
ctcgtcatcg ttgttgcggc caacctaatt tatcatggag gagtagtgcc agggatttca    780
cgtttggcgt acttctggtg cttaattaat ttatttgggg ttttgtattt taaaattagg    840
taaaatttct ataattttac aaaaattaac ttatttatt aaaaattaaa agatttagac     900
taaatagcaa atcacgcaa tgggtttagt gttttaatac gagattagac ataataataa     960
taacacctga tggtcctcta ttttcaatta tttgccaact aaaccacaat caaccatgtt   1020
caacacaatt ggaattctac tgatatatca ttacagctgc caaaacattt atttaggcca   1080
ttaatcaatt ttaattgaac atgctatttt tctatcatca attcagcttc ttttttttata  1140 ttaatttaat ttataattaa cactaatgac aaaattagat attaaatta tgagaatgaa    1200 acataaaatt aatatataaa aaatatatta gttttaaaaa taattttaaa tattaaactc   1260
aaaatattat atatatatat atatatatat atatatgaaa ttaaaatttt aaattaaaaa   1320
```

```
aatgcagtaa aaaaaaaaaa aataataaag tagctattgg atccaagggt ggtttagaac    1380
gctactcgtg cgaagcaaga gtgaggaaaa tgccaaggac ccgtcacgca cgccacatgt    1440
gtggggagga ggctcccgtt ctcgcattct tataaaaatg tcccagatcc aaatctcctg    1500
aaactaagct catcattccc tcttcctcct ctccctttct ctctcctgcg ccggcatatt    1560
tttac                                                                1565

<210> SEQ ID NO 22
<211> LENGTH: 1352
<212> TYPE: DNA
<213> ORGANISM: Hevea brasiliensis

<400> SEQUENCE: 22
gcagccggtt tggtctgaaa ttgcagatcc gagcgatgat cgaattttca cgaaataaaa      60
tgaaagtaca tacgcgaagt ccacaataac agggttagaa taatatatat atatatatat     120
atatatatta tttttaaata attattatat atatataata ataattattt aaaaattaag     180
aatgttacac aagtgatgat atattgaaat tttataataa attaaataat cacatgtaaa     240
attaataaca tgtataaatt gagatattac ttttattcat gctatattta ttttttactt     300
taaaaattct tttttttaa tataaaatta ttaaaatata aattcttaat tttctactta      360
taaaacatat actaatattg gaactatta caatgtcatc tcattttat tattattatt       420 tttttttata gttcatcttc caattaaaaa gggtaattta caaaatcaca atgaaagaaa     480
tgatgatcat gactatataa taaattaatg atatttaagg taataaaaaa aaaacatgaa     540
agtaacataa caaaaagatt ataaagagt cttgatgcac ataaggtaac atttccttcc      600
tcacaaaaat tttttttttt taatataaaa aataatttttt ttataaatat aggtgaatca    660
gatgcacata atctctttaa catatatata tatatatata tctaagaaaa aagaaatcaa     720
gaatttatct tttatttccc cattgctaga aaatcagtgc agttactggc tcaacccatt     780
atactgtcag ggttttgcaat tgtggacttt ttatcatcaa tttaggcttt taatcaaccg    840
gataatctgg ttcattttttc cttatttta agatacataa atgggagagt tactataaaa     900
ttcgattaga tttcaaatta aaataaaata ttttcttatt aaaaaagatt taaatttaaa     960
tttggttaga atcaaattga accaaagcag ataaatcaaa atagaatcaa agaattctat    1020
ggtctggtat caaaaaccgg ctcagaccaa accggctgcc agcctacttc cacaaccccca   1080 tatatcatag atgtcccttt acataaacgc aaaacaagaa cataaaaatg tctctcacca    1140
ctcgccttct aaatgcccac gtgggtagcg ccaccaccag actctcgtcc tcgcttccct    1200
cctctgcttc tcctcgttat tctcactttc tctctaccca atttgcctct ccttctctca    1260
ttcaattccc tctaactctt aaaccttcgt ctacctcttc gttatctagg gtattttcgt    1320
cttctccatc tgcaatcacc gctacttcca cc                                  1352

<210> SEQ ID NO 23
<211> LENGTH: 533
<212> TYPE: DNA
<213> ORGANISM: Hevea brasiliensis

<400> SEQUENCE: 23
cgtggctaga ttattctagg atttgggtat cgcataattt ttagttacta gtgtttagag      60
ttgcttatat ccaataactt cttaataaca atttttaaata aaaatattc ttgtgcgtat     120 caaaaaaatt taaataaaaa ccatgacata ttcaatttcc ttaactaggt taaaaatttt     180
tcatgcatta gcatatactt aatttgttga taaatagacc tttgatcaac tctcaacatg     240
```

```
accaaagtcc ctccttttt  tagtataatt ggtttcaatt gaaagtcgaa ctctagactt      300
tatagtttat gaaatgattt caatactact gggttaatgc tcattggtca aagtactcac      360
agcagtatca agtagtcttt taaggttaaa aaaacttata tatatattaa cgaaagatgc      420
cacttgattt agtgtcacct ccgaaataat caacttaatt tagttattgg atctgagatt      480
ttatttttat attttttttc tgatgagcag gttaagtcag tggtttaagt aaa             533

<210> SEQ ID NO 24
<211> LENGTH: 919
<212> TYPE: DNA
<213> ORGANISM: Hevea brasiliensis

<400> SEQUENCE: 24
aaccgtccac caatctttga gttccagtga gtcatctact ggttgcttga cagatccatc       60
aataaaacca tatttctttt tggcccgtaa tgcagtcagc atagctcgcg cccattcttc      120
gtaattctcg cccttcaact gaacttgggt aatcaagtta tctgggttgt cattcgaatt      180
cagtgtttaa gaactaaaag ttttcttccc tgatccagaa ctctcatttt tcttttcatc      240
aaccatggct ctgataccat gtaaaaaaac taagaaattt tggaataaga attcttatct      300
ttattgcccc agaaataaaa tatatatata aaaaaattac agctaacaaa taggtcccta      360
atcaagctaa actaccaaaa ttgtatcaaa gtcatacaac aaaaggtaaa aacagatatg      420
cacacaaaaa ttcctaaaca aatgccctaa ataaatacaa aataagtgac agctaacagc      480
tgcatttcca ataattaatt taactaataa aatttataat cttaaaaata attttaatat      540
tattgaatta aaatttataa ataaaattaa cactgttaaa attaaaagaa aattattaag      600
atttgaattt ttaagcggtt atttaatttt gaaaaacaag gctaactttt ttttttatat      660
aatttactaa aaaattcatg aatgaaaaaa aaaaatccat aagtaaactt accccatacg      720
ggttatgcac gctaaaccaa taaaacagaa acacgtttat acactcgttt tcatttccat      780
ctataaatag agagatttgt ttttagtttt aaaccataat cagttgatag cttccacagt      840
gttttccgaa aggcaaatct tttttcaaac ttcagcgact gcgttttgaa tttgtgatt       900 ttaaaggaaa ttttcaatt                                                   919
```